(12) United States Patent
Liu et al.

(10) Patent No.: US 8,466,259 B2
(45) Date of Patent: *Jun. 18, 2013

(54) ADJUVANTS

(75) Inventors: Shih-Jen Liu, Miaoli County (TW);
Hsueh-Hung Liu, Miaoli County (TW);
Chih-Hsiang Leng, Miaoli County
(TW); Hsin-Wei Chen, Miaoli County
(TW); Yan Chak Kwok, Miaoli County
(TW); Pele Choi-Sing Chong, Miaoli
County (TW)

(73) Assignee: National Health Research Institutes,
Miaoli County (TW)

( * ) Notice: Subject to any disclaimer, the term of this patent is extended or adjusted under 35 U.S.C. 154(b) by 247 days.

This patent is subject to a terminal disclaimer.

(21) Appl. No.: 12/702,567

(22) Filed: Feb. 9, 2010

(65) Prior Publication Data

US 2010/0166785 A1 Jul. 1, 2010

Related U.S. Application Data

(63) Continuation-in-part of application No. 12/329,026, filed on Dec. 5, 2008, now Pat. No. 8,426,163, which is a continuation-in-part of application No. 12/331,576, filed on Dec. 10, 2008, now Pat. No. 7,833,776.

(60) Provisional application No. 61/012,263, filed on Dec. 7, 2007, provisional application No. 61/013,206, filed on Dec. 12, 2007.

(51) Int. Cl.
*C07K 1/00* (2006.01)
*A61K 39/00* (2006.01)

(52) U.S. Cl.
USPC ........................ 530/350; 424/184.1

(58) Field of Classification Search
None
See application file for complete search history.

(56) References Cited

U.S. PATENT DOCUMENTS

| | | |
|---|---|---|
| 4,745,069 A | 5/1988 | Mayne et al. |
| 5,942,236 A | 8/1999 | Lobet et al. |
| 6,013,258 A | 1/2000 | Urban et al. |
| 6,183,746 B1 | 2/2001 | Urban et al. |
| 6,361,966 B1 | 3/2002 | Walker et al. |
| 6,538,118 B1 | 3/2003 | Huebner et al. |
| 6,582,704 B2 | 6/2003 | Urban et al. |
| 6,936,263 B2 | 8/2005 | Revets et al. |
| 7,097,843 B2 | 8/2006 | Urban et al. |
| 7,235,243 B2 | 6/2007 | Becker et al. |
| 7,314,629 B2 | 1/2008 | Zagury et al. |

(Continued)

FOREIGN PATENT DOCUMENTS

| | | |
|---|---|---|
| CA | 2183416 | 8/1995 |
| CA | 2706101 | 6/2009 |

(Continued)

OTHER PUBLICATIONS

Sung et al., Biochemical characterizations of *Escherichia coli*-expressed protective antigen Ag473 of *Neisseria meningitides* group B., Vaccine. Nov. 29, 2010, vol. 28(51), pp. 8175-8182.*

(Continued)

*Primary Examiner* — Alexander Kim
(74) *Attorney, Agent, or Firm* — Occhiuti Rohlicek & Tsao LLP

(57) ABSTRACT

Disclosed are lipopeptides or lipoproteins, related compositions, and related methods.

14 Claims, 17 Drawing Sheets

U.S. PATENT DOCUMENTS

| | | | |
|---|---|---|---|
| 7,569,225 | B2 | 8/2009 | Jackson et al. |
| 7,833,776 | B2 | 11/2010 | Leng et al. |
| 2005/0276813 | A1 | 12/2005 | Muhlradt et al. |
| 2005/0281835 | A1* | 12/2005 | Yang .......................... 424/185.1 |
| 2009/0074781 | A1 | 3/2009 | Chen et al. |
| 2009/0081253 | A1 | 3/2009 | Hanon et al. |
| 2009/0176273 | A1 | 7/2009 | Leng et al. |
| 2009/0221499 | A1 | 9/2009 | Leng et al. |
| 2010/0303849 | A1* | 12/2010 | Chen et al. ................. 424/192.1 |
| 2010/0322953 | A1* | 12/2010 | Leng et al. ................. 424/186.1 |
| 2012/0041179 | A1* | 2/2012 | Hsieh et al. .................. 530/359 |

FOREIGN PATENT DOCUMENTS

| | | |
|---|---|---|
| CN | 1793335 | 6/2006 |
| EP | 1612218 | 1/2006 |
| EP | 2058002 | 5/2009 |
| GB | 2001/029236 | 4/2011 |
| JP | 2008-113608 | 5/2008 |
| WO | 92/05248 | 4/1992 |
| WO | 92-16636 | 10/1992 |
| WO | 99/10375 | 3/1999 |
| WO | 99/57280 | 11/1999 |
| WO | WO01/00790 | 1/2001 |
| WO | 2004/052395 | 6/2004 |
| WO | 2007/199896 | 10/2007 |
| WO | WO 2008/049329 | 5/2008 |
| WO | 2008/079372 | 7/2008 |
| WO | 2010/148496 | 12/2010 |

OTHER PUBLICATIONS

PeptideCutter for SEQ ID No. 1 (last viewed on Mar. 7, 2012).*
Shu et al., Core Structure of the Outer membrane Lipoprotein from *Escherichia coli* at 1.9Å Resolution., (2000), vol. 299, pp. 1101-11112.*
Babaeipour, Valiollah, et al. "Enhancement of human granulocyte-colony stimulating factor production in recombinant *E. coli* using batch cultivation" Bioprocess Biosyst Eng (2010) pp. 591-598.
Chen, H-W. et al. A novel technology for the production of a heterologous lipoprotein immunogen in high yield has implications for the field of vaccine design. Vaccine. Epub: IS Jan. 2009 (Jan. 15, 2009). vol. 27, pp. 1400-1409.
Chiung-Yi Huang. "Potential Treatment of Human Papillomavirus Associated Tumors Using Recombinant Inactive-E7 Lipoproteins." Electronic Theses & Dissertations Services; Master Programs of Life Sciences, Aug. 24, 2009. pp. 1-5.
Cullen et al., "Construction and Evaluation of a Plasmid Vector for the Expression of Recombinant Lipoproteins in *Escherichia coli*," Plasmid 49: 18-29 (2003).
De et al., "Purification and Characterization of *Streptococcis pneumoniae* palmitoylated and pneumococcal surface adhesion A expressed in *Escherichia coli*," Vaccine: 18: 1811-1821 (2000).
Dumon-Seignovert et al., The toxicity of recombinant proteins in *Escherichia coli*: a comparison of overexpression in BL21 (DE3), C41 (DE3), and C43(DE3)., Protein Expression and Purification, vol. 37, Issue 1, Sep. 2004, pp. 203-206.
*E. coli* genotypes (last viewed on Feb. 1, 2011).

Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.
Green et al., The e(P4) Outer membrane Protein of Haemophilus influenzae: biologic activity of Anti-e Serum and Cloning and Sequencing of the Structural Gene., Infection and Immunity, 1991, vol. 59, pp. 3191-3198.
Hsu, C-A. et at. Immunoproteomic identification of the hypothetical protein NMB1468 as a novel lipoprotein ubiquitous in *Neisseria meningitidis* with vaccine potential. Proteomics. 2008. vol. 8, pp. 2115-2125.
Kamalakkannan et al., "Bacterial Lipid Modification of Proteins for Novel Protein Engineering Applications," Protein, Engineering, Design & Selection 17(10): 721-729 (2004).
Legrain et al., "Production of Lipidated Meningococcal Transferrin Binding Protein 2 in *Escherichia coli*" Protein Expression and Purification 6:570-578 (1995).
Liu, et al. "Structure of the Human Papillomavirus E7 Oncoprotein and its Mechanism for Inactivation ofthe Retinoblastoma Tumor Suppressor", 1. Biol. Chem., Jan. 2006. vol. 281, pp. 578-586.
Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998. pp. 2103-2109.
Rezwan, et al. "Lipoprotein synthesis in mycobacteria" *Microbiology*. Mar. 2007, vol. 153, pp. 652-658.
Wikman, et al. General strategies for efficient adjuvant incorporation of recombinant subunit immunogents. *Vaccine*. (2005), vol. 23, pp. 2331-2335.
Cote-Sierra, et al. "A New Membrane-Bound Oprl Lipoprotien Expression Vector High Prodcution of Heterologous Fusion Proteins in Gram (−) Bacteria and the Implications for Oral Vaccination" *Gene* (1998) vol. 221, pp. 25-34.
Crill, Wayne D., et al. "Monoclonal Antibodies That Blind to Domain III of Dengue Virus E Glycoprotien Are the Most Efficient Blockers of Virus Adsorption to Vero Cells" *Journal of Virology* (Aug. 2001) pp. 7769-7773.
Chen, W., et al. "Induction of cytotoxic T-lymphocytes and antitumor activity by a liposomal lipopeptide vaccine" *Mol. Pharm.* vol. 5, No. 3 (2008) pp. 464-471.
Jackson, D.C., et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.
Masconi, et al. "Structural Basis for the Immunogenic Properties of the Meningococcal Vaccine Candidate LP2086" The Journal of Biological Chemistry, vol. 284, No. 13, pp. 8738-8746 (Mar. 27, 2009).
Sivashanmugam, Arun, et al. "Practical protocols for production of very high yields of recombinant proteins using *Escherichia coli*" Protein Science vol. 18, pp. 936-948 (2009).
Chiung-Yi Huang et al. "Recombinant Lipidated HPV E7 Induces a TH-1-Biased Immune Response and Protective Immunity against Cervical Cancer in a Mouse Model," PLoS One, 7(7) e40970-e40970 (2012).

* cited by examiner

ADJUVANTS

RELATED APPLICATIONS

This application is a continuation-in-part of (A) U.S. patent application Ser. No. 12/329,026, filed on Dec. 5, 2008, which claims priority to U.S. provisional application No. 61/012,263, filed on Dec. 7, 2007; and (B) U.S. patent application Ser. No. 12/331,576, filed on Dec. 10, 2008, which claims priority to U.S. provisional application No. 61/013,206, filed on Dec. 12, 2007. The contents of these prior applications are herein incorporated by reference.

BACKGROUND

Vaccination is considered to be the most effective and efficient approach to prevent pathogen infection. However, there are still many infectious diseases for which no vaccine is yet available or adequate immunization cannot be achieved. In addition, many vaccines are inadequate because of low efficiency, serious side effects, low stability or high costs. Thus, there is a great need for more effective vaccines and related reagents.

A vaccine contains a pathogen-derived antigenic material, e.g., protein, for inducing protective immune responses. In general, modified proteins, such as lipidated proteins, are more immunogenic than unmodified proteins. Proteins in certain vaccine products have been prepared by expression in *E. coli* using recombinant technology. However, *E. coli* is generally viewed as not suitable for producing modified proteins, particularly, lipidated proteins. More specifically, *E. coli* cells lipidate poorly naturally lipidated proteins and do not produce non-naturally lipidated proteins in lipidated form.

SUMMARY

This invention is based, at least in part, on unexpected discoveries (1) that a lipidating sequence of Ag473 led to lipidatation of a fusion protein having the lipidating sequence and (2) that the lipidated fusion protein or its fragment was not only highly immunogenic itself but also can enhance the immunogenicity of other antigens.

The above-mentioned Ag473 is a *Neisseria Mengitidis* lipoprotein consisting of four domains, SP and Domains 1-3. Shown below is the lipidating sequence in the amino acid sequence of this protein (SEQ ID NO: 1) with the four domains identified:

SP: amino acid residues 1-17 in SEQ ID NO:1 (underlined, SEQ ID NO: 2)

Domain 1: amino acid residues 18-40 in SEQ ID NO:1 (highlighted, SEQ ID NO: 3)

Domain 2: amino acid residues 41-71 in SEQ ID NO:1 (bold face, SEQ ID NO: 4)

Domain 3: amino acid residues 72-121 in SEQ ID NO:1 (italic, SEQ ID NO: 5)

D1: amino acid residues 1-40 in SEQ ID NO:1 (SEQ ID NO: 6)

D2: amino acid residues 1-71 in SEQ ID NO:1 (SEQ ID NO: 9)

D3: amino acid residues 1-121 (SEQ ID NO: 1)

One aspect of this invention features an isolated lipopeptide, lipopolypeptide, or lipoprotein having the structure of formula (I):

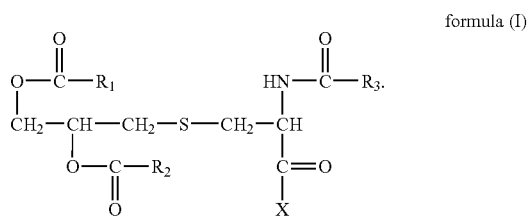

formula (I)

One of $R_1$, $R_2$, and $R_3$ is $C_{14-20}$ alkenyl, and each of the others, independently is $C_{14-20}$ alkyl or $C_{14-20}$ alkenyl; X is an amino acid sequence that is 1-100 (e.g., 2-50, 3-20, or 5-15) amino acid residues in length. For example, $R_2$ can be $C_{14-20}$ alkenyl. Each of $R_1$ and $R_3$ can be $C_{14-20}$ alkyl. In one embodiment, $R_2$ is —$(CH_2)_7$—CH=CH—$(CH_2)_5CH_3$. In another, each of $R_1$ and $R_3$ is —$(CH_2)_{14}$—$CH_3$. In another embodiment, the lipopeptide or lipoprotein has the following configuration:

```
Met Lys Lys Leu Leu Ile Ala Ala Met Met Ala Ala Ala Leu Ala Ala Cys Ser
1               5                   10                  15
Gln Glu Ala Lys Gln Gly Val Lys Glu Ala Val Gln Ala Val Glu Ser Asp Val
        20                  25                  30                  35
Lys Asp Thr Ala Ala Ser Ala Ala Glu Ser Ala Ala Ser Ala Val Glu Glu Ala
                40                  45                  50
Lys Asp Gln Val Lys Asp Ala Ala Ala Asp Ala Lys Ala Ser Ala Glu Glu Ala
55                  60                  65                  70
Val Thr Glu Ala Lys Glu Ala Val Thr Glu Ala Lys Glu Ala Val Thr Glu Ala
        75                  80                  85                  90
Lys Glu Ala Val Thr Glu Ala Lys Asp Thr Leu Asn Lys Ala Ala Asp Ala
                95                  100                 105
Thr Gln GLu Ala Ala Asp Lys Met Lys Asp Ala Ala Lys
    110                 115                 120
```

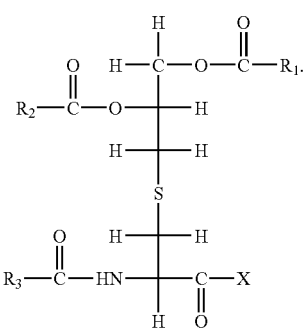

In particular, the lipopeptide is

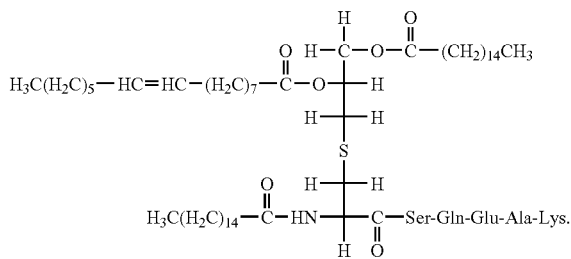

The N-terminus of X can be linked to the carbonyl group adjacent to X shown in formula (I). X can be 3-20 amino acid residues in length. In one example, X has the sequence of SQEAK or SQEAKQEVK (SEQ ID NO: 7 or 8). For example, the lipoprotein/peptide can be Lipo-CSQEAK or Lipo-CSQEAKQEVK (SEQ ID NO: 11 or 10).

In one embodiment, one of $R_1$, $R_2$, and $R_3$ is $C_{14-20}$ alkenyl, and each of the others, independently is $C_{16-20}$ alkyl or $C_{16-20}$ alkenyl. For example, one of R2 or R3 is $C_{14-20}$ alkenyl, and R1 is $C_{16}$ alkyl.

The term "alkyl" refers to a saturated, linear or branched hydrocarbon moiety. Unless specified otherwise, it includes 1-30 carbon atoms. Examples of alkyl includes, but are not limited to, $(CH_2)_{13}CH_3$, —$(CH_2)_{15}CH_3$, —$(CH_2)_{17}CH_3$, and —$(CH_2)_{19}CH_3$.

The term "alkenyl" refers to a linear or branched hydrocarbon moiety that contains one, two, three, or even more double bonds. Unless specified otherwise, alkenyl includes 2-30 carbon atoms. Examples of alkyl includes, but are not limited to, —$(CH_2)_7$—CH=CH—$(CH_2)_5CH_3$.

Alkyl and alkenyl mentioned herein include both substituted and unsubstituted moieties. Possible substituents include, but are not limited to, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester.

This invention also features (1) an adjuvant composition comprising or consisting essentially of the above-mentioned lipo-peptide or lipo-protein, and (2) an immunogenic composition containing an antigen and the lipopeptide or lipoprotein. Also featured is a method of inducing an immunological response in a subject by administering to a subject in need thereof an antigen and the lipopeptide or lipoprotein.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds. In a preferred embodiment, the subject is a human. In another embodiment, the subject is an experimental animal or animal suitable as a disease model.

Within the scope of this invention is a method of preparing the above-mentioned lipopeptide or lipoprotein. The method includes providing a host *E. coli* cell containing a nucleic acid encoding a protein that has a first segment having a lipidating sequence that includes the sequence of SEQ ID NO: 3 or SEQ ID NO: 1, 6, 7, 8, or 9, cultivating the *E. coli* cell in a medium under condition permitting expression of the protein in lipidated form; and purifying the lipidated form of the protein from the cell or the medium. Alternatively, the nucleic acid can be transcribed and translated in vitro, for example, using T7 promoter regulatory sequences and T7 polymerase in cell lysate from, e.g., *E. coli*. One exemplary lipidated fusion protein can include, from N-terminus to C-terminus, SP and D1 domains of Ag473 (D1) and dengue envelope protein domain III (E3). This recombinant lipid protein is named rlipo-D1E3. The method can further include a step of incubating the lipidated form of the protein with a protease to generate the lipopeptide, e.g., lipo-Nter as descried in the examples below. The nucleic acid can be heterologous to the cell.

An isolated protein, polypeptide or peptide refers to a protein, polypeptide, or peptide substantially free from naturally associated molecules, i.e., it is at least 75% (i.e., any number between 75% and 100%, inclusive) pure by dry weight. Purity can be measured by any appropriate standard method, e.g., by column chromatography, polyacrylamide gel electrophoresis, or HPLC analysis. An isolated peptide, polypeptide or protein can be purified from a natural source, produced by recombinant DNA techniques, or by chemical methods.

The terms "protein" and "polypeptide" are used herein interchangeably to describe any chain of amino acids, regardless of length or post-translational modification (for example, glycosylation or phosphorylation). Thus, the term "polypeptides of the invention" includes: full-length, naturally occurring proteins of the invention; recombinantly or synthetically produced polypeptides that correspond to full-length naturally occurring proteins of the invention; or particular domains or portions of the naturally occurring proteins. The term also encompasses mature polypeptides that have an added amino-terminal methionine (useful for expression in prokaryotic cells). A peptide refers to chains that are short enough to be made synthetically from the constituent amino acids. Generally, a peptide is 50 amino acid residues in length or shorter (e.g., 50, 40, 30, 20, 10, or 5 residues in length).

A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
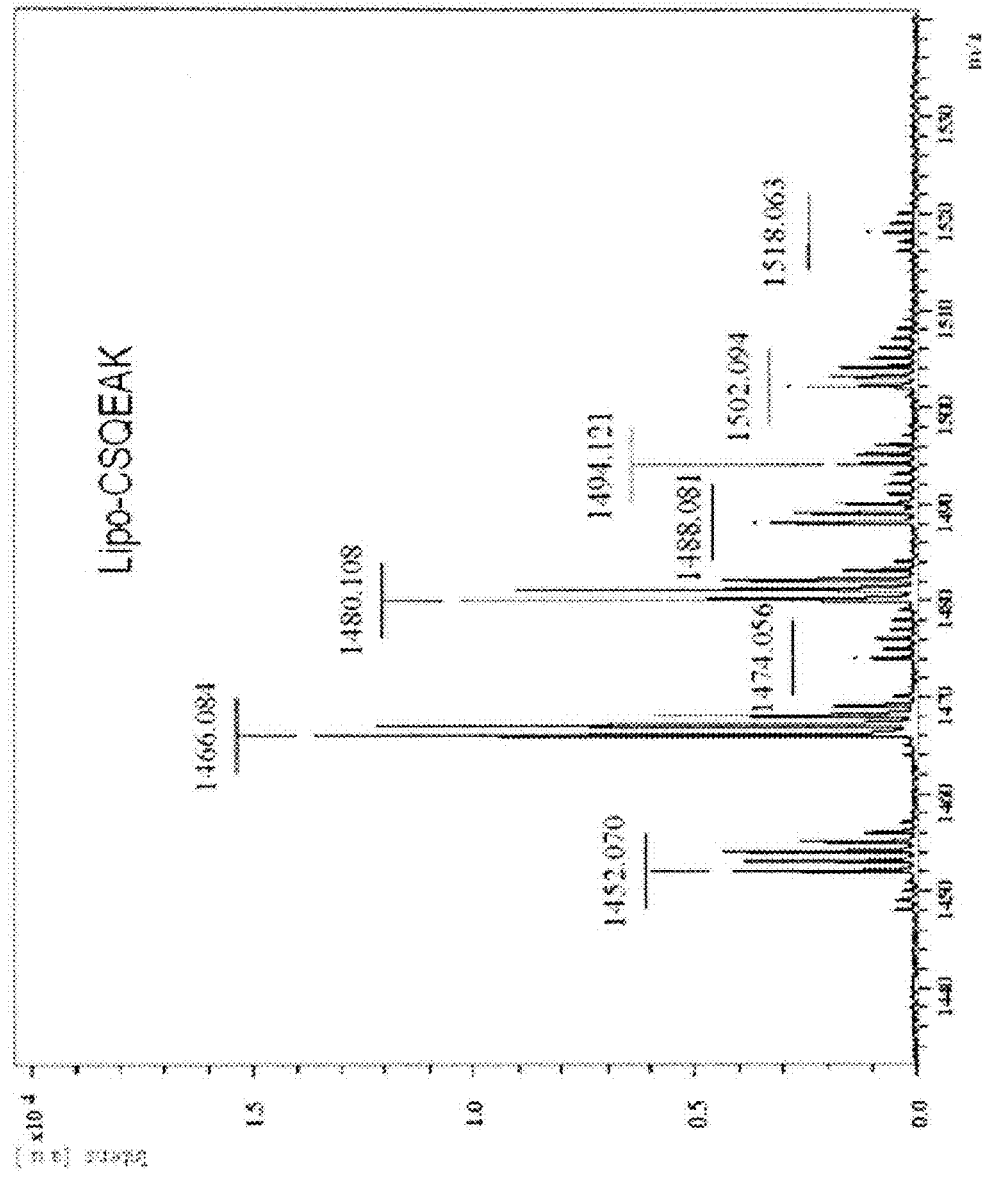
FIGS. 1a and b are diagrams showing identification (a) and separation (b) of lipo-Nter (Lipo-CSQEAK, SEQ ID NO: 11) derived from rlipo-D1E3 using MALDI-TOF mass spectrum.

This invention relates to novel lipoproteins or lipopeptides, which can be used as an adjuvant for enhancing the efficacy of a vaccine. Lipid moieties at the N-terminals of the lipoproteins or lipopeptides contribute to the adjuvant activity. The lipid moieties could be a diacyl or triacyl lipid.

The lipoprotein can be made using a lipidating sequence. The term "lipidating sequence" refers to a non-naturally occurring amino acid sequence that (a) includes a first fragment that is at least 80% (85%, 90%, 95%, or 99%) identical to SP of Ag473 and a second fragment at least 80% (85%, 90%, 95%, or 99%) identical to Domain 1 of Ag473, the first fragment being at the N-terminus of the lipidating sequence, and (b) facilitates lipidation in *E. coli* of a polypeptide or protein carrying the lipidating sequence at its N-terminus (i.e., a fusion protein). In the lipidating sequence, the first fragment is linked to the second fragment either directly or via a peptide linker. Preferably, this sequence has a maximum length of 40-100 (e.g., 40-80) amino acids. In one example, the lipidating sequence described herein includes SP and Domain 1.

As used herein, "percent homology" of two amino acid sequences is determined using the algorithm described in Karlin and Altschul, *Proc, Natl. Acad. Sci. USA* 87:2264-2268, 1990, modified as described in Karlin and Altschul, *Proc, Natl. Acad. Sci. USA* 90:5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used.

A "peptide" refers to the arrangement of amino acid residues in a polymer. A peptide can be composed of the standard 20 naturally occurring amino acid, in addition to rare amino acids and synthetic amino acid analogs. A "recombinant peptide" refers to a peptide produced by recombinant DNA techniques; i.e., produced from cells transformed by an exogenous DNA construct encoding the desired peptide. A "synthetic peptide" refers to a peptide prepared by chemical synthesis.

The above-mentioned fusion protein can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant lipoprotein or lipopeptide of this invention.

In one embodiment of the present invention, the lipidating sequence mentioned above is linked to dengue cED III to form a fusion protein, rlipo-D1E3, which is in lipidated form when expressed in *E. coli* by conventional recombinant technology. An example follows. A DNA fragment encoding the lipidating sequence and a DNA fragment encoding the dengue cED III are inserted into an expression vector, preferably carrying a strong promoter (e.g., T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured under suitable conditions for protein expression. It is preferred that the *E. coli* host strain be resistant to the toxic effects induced by over-expression of exogenous proteins. Such *E. coli* strains can be identified/generated by the methods described in U.S. Pat. No. 6,361,966. Examples of these *E. coli* strains include, but are not limited to, C43(DE3) (ECCC B96070445), C41 (DE3) (ECCC B96070444), C0214(DE3), DK8(DE3)S (NCIMB 40885), and C2014(DE3) (NCIMB 40884).

Preferably, the fusion protein thus expressed is isolated from the *E. coli* host cells and its lipidation status is confirmed via methods known in the art, e.g., immunoblotting with an anti-lipoprotein antibody or mass spectrometry.

The fusion protein can be further subject to protease treatment to generate smaller lipid proteins or peptides. These lipid proteins or peptides can used as adjuvant in an immunogenic composition (e.g., a vaccine) for generating antibodies against various antigens in a subject (e.g., a human subject). Such compositions can be prepared, e.g., in the manners described below, or by any other equivalent methods known in the art.

Mycobacterial lipoproteins affect both innate and adaptive immunities. They have been shown to induce antimicrobial activity and trigger host defense mechanisms through Toll-like receptors. Furthermore, several mycobacterial lipoproteins, have been demonstrated to be an important inducers of activation of humoral and cellular immune responses against mycobacteria. Besides eliciting the activation of the immune system, lipoproteins have been identified as major antigens of *M. tuberculosis, Mycoplasma hyorhinis*, and *Treponema pallidum*.

An outer surface protein (OspA) of *Borrelia burgdorferi* is a Braun lipoprotein (BLP). OspA is a 31 kDa monomeric protein anchored to the membrane via a lipidated N-terminal cysteine. It has been shown that immunization with full-length OspA can protect mice, dogs, and rhesus monkeys against *B. burgdorferi*. However, the protection of nonlipidated OspA protein was incomplete and unable to elicit protective immunity to *B. burgdorferi* (Bockenstedt et al. 1993, *J Immunol* 151: 900-906; Johnson et al. 1995, *Vaccine* 13: 1086-1094). In 1998, the recombinant lipoprotein, OspA was approved by US FDA as the first Lyme disease vaccine (LYMErix, SmithKline Beecham). Although OspA is an effective vaccine, the use of full-length Osp A as a vaccine raised concerns about the risk of autoimmune responses (Gross et al. 1998, *Science* 281: 703-706) and the vaccine was discontinued.

Besides the OspA, it has been demonstrated that BLPs are as active as lipoppolysaccharide (LPS) in stimulating human endothelial cell to an inflammatory phenotype. However, unlike the LPS, the tolerance induced by BLP protects mice against LPS, live bacteria, and polymicrobial sepsis induced lethality. In contrast, the LPS tolerance affords protection only against the lethal effects of LPS.

N-acyl-S-diacylglyceryl-cystinyl modification of bacterial protein has been elucidated by Braun in 1973. Subsequently, the Braun lipoproteins (BLP) have been identified in all bacteria (Madan Babu and Sankaran 2002, *Bioinformatics*) and could be the structural proteins, enzymes, receptors or transporters performing essential functions at the membrane-aqueous interfaces. However, many lipoproteins have been identified in various bacteria that lost their N-terminal fatty acid to produce di-acylated lipid. Both di- or tri-acylated lipoprotein have been shown that can activate Immune responses through TLR2-mediated signaling pathway. TLR2 forms heterodimers with either TLR1 or TLR6 according to the length of N-terminal fatty acid chain and the charge of the C-terminal amino acid, indicating that different lipid structures of the N-terminal portions of bacterial lipoproteins could induce differential down-stream gene expression and lead to regulate immune responses.

*E. coli* expression systems, including kinds of variant strains, have been widely used in producing homologous and/or heterlogous proteins. However, the over-expression of lipoproteins in *E. coli* with divergent lipoprotein signal peptides often results in incomplete modification or entirely absence of lipid moiety. Poor lipid modification could be improved by fusing the target gene with different signal peptides. These approaches could increase the expression level of lipoprotein to being detected by immunoblot or to 3% of total cell protein. Yet, to over-express recombinant lipoproteins at high level is still a challenge and hurdle for producing recombinant lipidated immunogens (lipo-immunogens).

To deal with the above-discussed challenge and hurdle, we developed a high-yield lipoprotein expression system and an essential leader sequence was also identified (see US Application 20090176273). This expression system was used to express heterogeneous lipoprotein that contains a dengue viral envelope protein domain 3.

This recombinant lipo-D1E3 (rlipo-D1E3) was produced and its biological function was characterized. The predicted N-terminal lipid structure that contains unsaturated fatty acid that is different from the well-known bacterial lipoproteins. The putative structure of lipid moisty contains a palmitoyl moiety at the N-terminal position, a palmitoyl, and an unsaturated fatty acid on the diacylglyerol residue. The rlipo-D1E3 could activate bone marrow derived dendritic cells to increase cytokines (IL-1α, IL-23, and IL-27) and chemokines (MIPα and MCP) RNA transcripts. The different gene expression profile could reflect the different immune regulatory effects.

As describe herein, the N-terminal portion of the rlipo-D1E3 (lipo-Nter) was obtained by digestion with trypsin and purification using liquid chromatography. The purified lipo-Nter was found to be able to activate bone marrow derived dendritic cells and activate NF-κB signaling through TLR2. In the presence of lipo-Nter, the mutant (or detoxic) HPV E7 protein immunization with mice could enhance both humoral (antibody titer) and cellular immune responses (anti-tumor effect). It was also found that the lipo-Nter could enhance anti-tumor effect of a CTL epitope peptide (derived from HPV E7 protein), its anti-tumor effects are stronger than the synthetic tripalmitoyl lipopeptide. These data show the purified lipo-Nter could be used as adjuvant to enhance both antigen-specific humoral and cellular immunity. In other words, the purified N-terminal fragment could be used as an adjuvant to enhance antibody titer and cytotoxic T lymphocytes killing effect.

It was unexpected that the lipid moiety of rlipo-D1E3 contains adjuvant activity. It was even more surprising that the purified N-terminal of rlipo-D1E3 could be combined with potential vaccine candidates to enhance either T or B cell immune responses. Therefore, this invention features an adjuvant that contains the recombinant lipoprotein or its N-terminal lipid moiety.

To produce a lipoprotein/polypeptide of this invention, one can culture a host cell in a medium under conditions permitting expression of a fusion protein/polypeptide encoded by a nucleic acid of this invention, and purify the fusion protein/polypeptide from the cultured cell or the medium of the cell. Alternatively, the nucleic acid of this invention can be transcribed and translated in vitro, for example, using T7 promoter regulatory sequences and T7 polymerase in cell lysate from, e.g., *E. coli*. The lipidated fusion protein can include, from N-terminus to C-terminus, D1 domain of Ag473 and dengue envelope protein domain III. The N-terminal lipid moiety can be obtained by digesting the rlipo-D1E3 using trypsin, and then purifying using reversed phase liquid chromatography (LC). It was found that the LC method was capable of separating lipopeptides differed by 14 amu using on-line mass analysis.

This above-described lipidated protein/peptide can be mixed with a pharmaceutically acceptable carrier such as a phosphate buffered saline, a bicarbonate solution to produce an adjuvant composition. As used herein, the term "adjuvant agent" or "adjuvant" means a substance added to an immunogenic composition or a vaccine to increase the immunogenic composition or the vaccine's immunogenicity. The term "vaccine" refers to any preparation intended for administration to a subject to produce or artificially increase immune response to a particular disease in the subject. Examples of vaccines include those described below.

The adjuvant of the invention can be used to enhance the immune response to an antigen of a vaccine formulation. The adjuvant of the invention can be used with antigens derived from any bacteria or from any virus, provided the antigen does not get destroyed or denatured. The adjuvant is also useful in vaccine compositions that contain an antigen as described in U.S. Pat. Nos. 5,616,328 and 5,084,269. It may be useful in conjunction with any material that raises either humoral and/or cell mediated immune response, such as, for example, live viral, bacterial, or parasitic antigens; inactivated viral, tumor-derived, protozoal, organism-derived, fungal, or bacterial antigens, toxoids, toxins; self-antigens; polysaccharides; proteins; glycoproteins; peptides; cellular vaccines; DNA vaccines; recombinant proteins; glycoproteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus* influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease. Especially, materials such as recombinant proteins, glycoproteins, and peptides that do not raise a strong immune response can be used in connection with the adjuvant of the invention.

In certain embodiments, the antigen may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, δ-catenin, γ catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ.-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

The adjuvant of the invention may be used in a vaccine formulation to immunize an animal. Thus, within the scope of this invention is an immunogenic or vaccine composition containing an antigenic agent and an adjuvant agent. The adjuvant agent contains the above-described lipoprotein/peptide and, once administered to a subject, enhances the subject's immune response to the antigenic agent. The term "immunogenic" refers to a capability of producing an immune response in a host animal against an antigen or antigens. This immune response forms the basis of the protective immunity elicited by a vaccine against a specific infectious organism. "Immune response" refers to a response elicited in an animal, which may refer to cellular immunity (CMI); humoral immunity or both. "Antigenic agent," "antigen," or "immunogen" means a substance that induces a specific immune response in a host animal. The antigen may contain a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin. The term "animal" includes all vertebrate animals including humans. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

In one embodiment, the vaccine formulation contains the adjuvant of the invention and an antigen. The optimal ratios of each component in the vaccine formulation may be determined by techniques well known to those skilled in the art.

A vaccine formulation may be administered to a subject per se or in the form of a pharmaceutical or therapeutic composition. Pharmaceutical compositions comprising the adjuvant of the invention and an antigen may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For purposes of this application, "physiologically acceptable carrier" encompasses carriers that are acceptable for human or animal use without relatively harmful side effects (relative to the condition being treated), as well as diluents, excipients or auxiliaries that are likewise acceptable. The carrier must be "acceptable" also in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. In one example, the lipidated protein is mixed with an antigen to form a composition useful for immune modulation. This composition may be prepared as injectables, as liquid solutions or emulsions. See U.S. Pat. Nos. 4,601,903; 4,599,231; 4,599,230; and 4,596,792.

Systemic formulations include those designed for administration by injection, e.g. subcutaneous, intradermal, intramuscular or intraperitoneal injection. For injection, the vaccine preparations may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 µg. Suitable dose range will vary with the route of injection and the size of the patient, but will typically range from about 0.1 mL to about 5 mL.

Other adjuvant can also be included in the adjuvant composition. Examples of such an adjuvant include, but are not limited to, cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery. See Audran R. et al. Vaccine 21:1250-5, 2003; and Denis-Mize et al. Cell Immunol., 225: 12-20, 2003.

Any of the above compositions may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders.

The above-described fusion proteins can be used in an immunogenic composition, e.g., a vaccine for generating antibodies and immune response against an antigen in a subject. A vaccine can be administered in a manner compatible with the dosage formulation, and in an amount that is therapeutically effective, protective and immuno-genic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

The dose of the composition depends, for example, on the particular polypeptide/protein, whether an additional adjuvant is co-administered, the type of adjuvant co-administered, the mode and frequency of administration, as can be determined by one skilled in the art. Administration is repeated as necessary, as can be determined by one skilled in the art. Sera or T-cells can be taken from the subject for testing the immune response elicited by the composition against the antigen of interest. Methods of assaying antibodies or cytotoxic T cells against a protein or infection are well known in the art. Additional boosters can be given as needed. By varying the amount of polypeptide/protein, the dose of the composition, and frequency of administration, the immunization protocol can be optimized for eliciting a maximal immune response. Before a large scale administering, efficacy testing is desirable. In an efficacy testing, a non-human subject (e.g., mouse, rat, rabbit, house, pig, cow, or monkey) can be administered via an oral or parenteral route with a composition of the invention. After the initial administration or after optional booster administration, both the test subject and the control subject (receiving mock administration) can be challenged with the antigen of interest to test the efficacy of the composition.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

In this example, TLR2 knockout (TLR2−/−) mice and TLR4-deficient mice were used to study the effector mechanisms and signaling pathways of a prototypic dengue vaccine lipo-immunogen (rlipo-D1E3) that has intrinsic adjuvant properties. Our results show that rlipo-D1E3 activates antigen-presenting cells through TLR2, but not through TLR4, and that the rlipo-D1E3-mediated initiation of the signaling pathway is similar to that of two other TLR2 agonists, Pam3 and the MALP-2 derivative, bisacyloxypropy-cystein (BPP-cysPEG) (Basinski et al. (2007) Int Arch Allergy Immunol 142, 91-8.). Interestingly, we found that rlipo-D1 E3 stimulated antigen-presenting cells could induce higher gene expression of cytokines and chemokines than Pam3 and BPP-cysPEG. These data indicated that different lipid moieties of TLR2 agonists may induce different cytokines or chemokines expression to regulate immune responses.

Materials and Methods

Reagents

All chemicals were from Sigma (St. Louis, Mo.) or Merck (Darmstadt, Germany). Restriction enzymes and ligase were from New England Biolabs, Inc. (Beverly, Mass.). Primers used for cloning came from Mission Biotech. Inc. (Taipei, Taiwan). Trypsin was purchased from Promega Co. (Madison, Wis.) and the matrix used for the mass spectrometry analysis was from Promega Co. (Madison, Wis.). The synthetic lipopeptide S-[2,3-bispalmitoyloxy-[2R]-propyl-[R]-cysteinyl-amido polyethyleneglycol (BPPcysPEGdef1375; BPPcysPEG) was a kind gift from Dr. M. Klein (AmVac, Switzerland) and Pam3CSK4 (N-palmitoyl-S-[2,3-bispalmitoyloxypropyl]cysteinyl-SKKKK [SEQ ID NO.: 12]) (Pam3) was purchased from InvivoGen (San Diego, Calif.). NF-κB-dependent promoter firefly luciferase was a kind gift from Dr. S.-F. Huang (National Health Research Institutes (NHRI), Taiwan), pRL-TK, a reporter plasmid that constitutively expresses Renilla luciferase was purchased from Promega Co. (Madison, Wis.), and Plasmid phTLR2flag was purchased from Addgene (Cambridge, Mass.).

Cell Lines and Mice

HEK293 cells (a human embryonic kidney cell line) were culture in DMEM supplemented with 10% FBS, 1% PS. TLR-4-deficient mice (C3H/HeJ) and TLR-2 knockout mice were purchased from Jackson Laboratory and held in Animal Center of NHRI. C57BL/6 and C3H/HeN were purchased from National Animal Center in Taiwan. All studies were approved by the Institutional Animal Care and Use Committee of the NHRI.

Production of Recombinant Lipo-Immunogen and Non-Lipidated Immunogen

Based on the consensus domain III of the dengue virus envelope protein (E3), the recombinant lipidated E3 immunogen (rlipo-D1E3) and its recombinant non-lipidated E3 (rE3) counterpart were prepared as described in Chen et al. (2009) *Vaccine* 27, 1400-1409 and Leng et al., (2009) *Microbes and Infection* 11, 288-295. Briefly, the E3 gene, either alone, or fused with a lipidation signal DNA sequence that encodes amino acid residues 1-40 in SEQ ID NO: 1 (SEQ ID NO: 6), was cloned into the vector pET-22b (+) and expressed in *E. coli* C43 (DE3) or BL21 (DE3). rlipo-D1E3 and rE3 were purified by immobilized metal affinity chromatography (IMAC), and the amount of residual lipopolysaccharide (LPS) was negligible (<3 EU/mg) in both preparations.

Mass Spectrometry

To analyze the Pam3 sample, 1 μl was mixed with an equal volume of a saturated solution of α-cyano-4-hydroxycinnamic acid (Sigma, St. Louis, Mo.) in acetonitrile (ACN)/0.1% trifluoroacetic acid (TFA) 1:3 (vol/vol). One microliter of the mixture was deposited on the target plate for further analysis. Purified rE3 and rlipo-D1 E3 were dialyzed against 25 mM ammonium bicarbonate, pH 8.5. Dialyzed samples were mixed with trypsin (Promega Co., Madison, Wis.) at a 50:1 ratio (wt/wt) in 25 mM ammonium bicarbonate, pH 8.5. The reaction was allowed to continue for 2 minutes at room temperature and was stopped by adding formic acid to a final concentration of 1.2%. The tryptic peptides were loaded into a ziptip that was washed with 100% ACN and pre-equilibrated with 0.1% TFA. The ziptip was washed stepwise with 0.1% TFA, 70% ACN/0.1% TFA, 100% ACN/0.1% TFA, and 100% ACN, by pipetting several times. The tryptic fragments were then eluted using 5 ul of 100% isopropanol and adjusted to a concentration of isopropanol of 50% after elution. One microliter of the eluted fragments was mixed with CHCA matrix and analyzed using a MALDI-TOF-TOF mass spectrometer (Bruker AutoFlex III smartbeam TOF/TOF200, Bruker Daltonics Inc. Billerica, Mass.)

Splenocytes Proliferation Assay

Splenocytes from C57BL6, TLR4-deficient C3H/HeJ, or TLR2-knockout (TLR2-/-) mice were suspended at a concentration of $2\times10^5$/well in 96-well plates and stimulated with lipopeptides or lipoproteins for 48 h at 37° C., 5% $CO_2$ in a humidified incubator. During the final 24 h of culture, 1 μCi of [3H]-thymidine was added to each well measure the synthesis of DNA, and the cells were harvested using a FilterMate automatic cell harvester (Packard, Meriden, Conn.). The radioactivity incorporated was determined in a TopCount microplate scintillation counter (Packard, Meriden, Conn., USA). LPS (0.01 μg/ml) was included in the assay as a positive control. All results are presented as the mean cpm±standard deviation (SD).

Preparation of Bone Marrow-Derived Dendritic Cells (BM-DCs)

BM-DCs were harvested as previously described in Lutz et al., (1999) Journal of Immunological Methods 223, 77-92. Briefly, femurs and tibiae of 6-8 week old female mice were removed, and the bone marrow cells were dispersed by vigorous pipetting. After removing red blood cells with lysis buffer, the isolated bone marrow cells were resuspended to a density of $2\text{-}5\times10^5$/ml cells with RPMI-10: RPMI-1640 (GIBCO BRL, Grand Island, N.Y.) supplemented with penicillin (100 U/mL, Sigma, St Louis, Mo.), streptomycin (100 μg/ml, Sigma), L-glutamine (2 mM, Sigma), 2-mercaptoethanol (50 μM, Sigma), and 10% heat-inactivated FBS. On days 0, 3, and 6, bone marrow cells were added to Petri dishes containing 200 U/mL (20 ng/ml) of recombinant granulocyte macrophage colony stimulating factor (MoGM-CSF, Peprotech, Rocky Hill, N.J.) in RPMI-10. At day 6, either LPS, rE3, rlipo-D1E3 or CpG was added at the indicated concentrations. Generally, immature dendritic cells made up 70% of the total cell population. Up-regulation of cell surface markers was analyzed using flow cytometry on a FACSCalibur (BD Biosciences, Franklin Lakes, N.J.) on gated CD11c+ cell populations.

Cytokine ELISA Assay

The production of cytokines by BM-DCs was determined using ELISA. BM-DCs were cultured either in medium alone, or in medium supplemented with LPS (100 nM), rlipo-D1E3 (100 nM), Pam3 (100 nM) or CpG (10 μg/mL). After a 24-hr incubation, the supernatants were harvested and analyzed for (a) TNF-α, (b) IL-6 and (c) IL-12 (p40) using ELISA. Briefly, 100 μL of anti-cytokine (10 μg/ml of IL-6, IL-12p40, TNF-α) antibodies (R&D system Inc. Minneapolis, Minn.) were coated onto 96-well microtiter plates with 0.1 M carbonate buffer, pH 9.6, following overnight incubation at 4° C. The coated plates were washed twice with 0.05% Tween 20 in PBS and then blocked with 5% non-fat milk in PBS at room temperature for 2 hours. Diluted supernatants from stimulated BM-DCs were applied to the coated wells at room temperature for 2 hours. Following the addition of biotin-conjugated, anti-cytokine antibodies (R&D system Inc. Minneapolis, Minn.), the assay was developed with 3,3',5,5'-tetramethylbenzidine (TMB), and the reaction was stopped by adding 100 µl of 1 M H2SO4 per well. The plates were read at 450 nm using an ELISA plate reader (Molecular Devices, CA). The production levels of the cytokines were calculated by subtracting the values obtained for non-stimulated groups.

NF-kB Luciferase Reporter Assay

HEK293 cells were plated onto 24-well plates ($2\times10^5$ cells/well) and cotransfected with 0.1 µg of pFLAG-TLR2, 0.01 µg of pNF-kB-luc, and 0.01 µg of the pRL-TK internal control plasmid (Promega, Madison, Wis.) using lipofectamine 2000 (Invitrogen, Carlsbad, Calif.). After 24 h, the transfected cells were stimulated with various synthetic lipopeptide or recombinant proteins for 24 h. The cells were lysed so that the luciferase activity could be measured using a dual-luciferase reporter assay system (Promega Co., Madison, Wis.). Firefly-luciferase activities were related to *Renilla*-luciferase activities for the purposes of normalization. Both firefly and *Renilla* luciferase activities were monitored using a Berthold Orion II luminometer (Pforzheim, Germany).

Western Blot Analysis

The BM-DCs were grown in DMEM or RPMI medium without FBS for 16-18 h and then stimulated with 100 nM of the indicated lipopeptides or lipoprotein for 10, 20, 40, 60, 90, or 120 minutes at 37° C. These treated BM-DCs were then lysed in 25 mM HEPES, 150 mM NaCl, 1 mM EDTA, 1 mM EGTA, 10% glycerol, 1% Triton X-100, 10 mM sodium pyrophosphate, 20 mM b-glycerophosphate, Na3VO4, 10 mM NaF, 10 mg/ml leupeptin, and 1 mM PMSF. The concentration of the protein lysates was determined using the BCA protein assay kit (Pierce, Rockford, Ill.). Fifty microgram of lysates were electrophoresed per lane of a 10% SDS-PAGE gel. After the resolved lysates in the gel were transferred to a PVDF membrane, the membranes were blocked with 5% milk and 0.05% Tween-20. The membranes were incubated with antibodies against p38, pp38, pERK1/2, or pJNK1/2 in 5% w/v BSA, 1×PBS and 0.1% Tween-20. Anti-p38 antibody was used as a control for the protein loading level in each lane. The membrane was developed using the LumiGLO® Chemiluminescent Substrate system (Millipore, Billerica, Mass.). The total p38 level was used for normalization, and the induction of pp38 was determined using image analysis software (Image J1.41, NIH, Bethesda, Md.). Relative phosphorylation was calculated as the (density of pp38/density of p38)× 100.

Real-Time Quantitative PCR (qPCR) Analysis of Gene Expression

The BM-DCs were purified using the Dynabeads® Mouse DC Enrichment Kit (Invitrogen Dynal AS, Oslo, Norway) according to the manufacturer's instructions to 60 90%. The purified BM-DCs were stimulated using medium alone, or with 100 nM of Pam3, BPPcysPEG or rlipo-D1E3, at 37° C. for 2 or 4 hours. Total RNA was extracted from the isolated cells using the RNeasy mini kit (Qiagen, Valencia, Calif.) following the manufacturer's instructions. RNA (0.5-1 µg) was reverse-transcribed to cDNA using an oligo-dT primer in a 20 µl volume and SuperScript III RT (Invitrogen, Carlsbad, Calif.). The mouse Universal Probe Library (UPL) set (Roche, Mannheim, Germany) was used to perform the real-time qPCR assay for gene expression in isolated cell populations (Liu et al. (2007) J Leukoc Biol 82, 354-360.). The specific primers and the UPL number were used as listed in the table below.

TABLE 1

The UPL number and primer sequences for mRNA analysis by real-time PCR. Sequences designed for the detection of indicated gene products by real-time PCR are presented.

| Gene name | UPL No. | Primers | SEQ ID NO.: |
|---|---|---|---|
| GADPH | 69 | Forward: 5'-ggagcggtagcacctcct-3' | 16 |
|  |  | Reverse: 5'-ctggttcatcatcgctaatcac-3' | 17 |
| IL-1α | 52 | Forward: 5'-ttggttaaatgacctgcaaca-3' | 18 |
|  |  | Reverse: 5'-gagcgctcacgaacagttg-3' | 19 |
| IL-23 | 6 | Forward: 5'-gagacactgatttgtgggaaaga-3' | 20 |
|  |  | Reverse: 5'-aaatgacacatgtaagattgctg-3' | 21 |
| IL-27 | 38 | Forward: 5'-catcgcatcacctctctgac-3' | 22 |
|  |  | Reverse: 5'-aagggccgaagtgtggta-3' | 23 |
| IL-10 | 3 | Forward: 5'-gctgccgtcattttctgc-3' | 24 |
|  |  | Reverse: 5'-tctcactggcccgtcatc-3' | 25 |
| IL-13 | 17 | Forward: 5'-cctctgacccttaaggagcttat-3' | 26 |
|  |  | Reverse: 5'-cgttgcacaggggagtct-3' | 27 |
| TGF-β1 | 72 | Forward: 5'-tggagcaacatgtggaactc-3' | 28 |
|  |  | Reverse: 5'-cagcagccggttaccaag-3' | 29 |

TABLE 1-continued

The UPL number and primer sequences for mRNA analysis by real-time PCR. Sequences designed for the detection of indicated gene products by real-time PCR are presented.

| Gene name | UPL No. | Primers | SEQ ID NO.: |
|---|---|---|---|
| MCP-1 | 62 | Forward: 5'-catccacgtgttggctca-3' | 30 |
| | | Reverse: 5'-gatcatcttgctggtgaatgagt-3' | 31 |
| MIP-1α | 40 | Forward: 5'-caagtcttctcagcgccata-3' | 32 |
| | | Reverse: 5'-ggactcttccggctgtagg-3' | 33 |
| CXCL1 | 75 | Forward: 5'-ttttgtatgtattagggtgaggacat-3' | 34 |
| | | Reverse: 5' gcgtgttgaccatacaatatgaa 3' | 35 |

The reaction mixture contained 5 ng cDNA, 0.2 µM primers, and LightCycler 480 Probe Master (Roche), and the reagents were reacted in a LightCycler 480 system (Roche). All qPCRs were carried out using an initial denaturation step at 95° C. for 10 min, followed by 45 cycles of 95° C. for 10 s, 60° C. for 20 s, and 72° C. for 2 s. Target gene expression was normalization to HPRT gene expression. The relative gene expression levels were calculated by comparing the expression levels after treatment with various stimulators to those obtained using medium alone. To compare the gene expression among the stimulators, the gene expression level was set as 1 for the control (medium alone) group.

Statistical Analysis

The statistical significance of differences between the experimental groups was determined using Student's t-test. The differences were considered statistically significant if the p value was <0.05.

Results

Lipid Moieties of rlipo-D1E3 and Pam3 are Different

Three major lipid modifications of rlipo-D1E3 were identified by mass spectrometry (Chen et al. (2009) Vaccine 27, 1400-1409.) In order to get more information about the lipid modifications, tryptic fragments of rlipo-D1 E3 were further purified and analyzed by MS/MS spectrometry. The masses of the lipid moieties in Pam3 and the purified fragments of rlipo-D1 E3 were calculated to analyze the differences in their lipid moieties. The molecular weight of Pam3 is 1509.6, and the y-ions could be identified after MS/MS analysis (FIG. 2a). Thus, the mass of the lipid-cysteinyl residue of Pam3 is 892.2 atomic mass units (amu), which confirms that the lipid moiety of Pam3 is palmitoyl-3-Cysteinyl (SNO6C54H102). On the other hand, five major peaks with m/z values of 1452.1, 1466.1, 1480.1, 1494.1 and 1502.1 were identified from the purified tryptic fragments of rlipo-D1E3 (FIG. 2b). Except for the peak with a value of 1502.1, the y-ions were determined after MS/MS analysis (FIGS. 2c-2f). The masses of the lipid-cysteinyl residues in the peaks of m/z 1452.1, 1466.1, 1480.1, and 1494.1 are found to be 890, 904, 918, and 932 amu, respectively. For the peak of m/z 1452.1, the mass of lipid-cysteinyl residue is 890 amu, 2 amu less than that of Pam3. This suggested that there is a double bond in its lipid moiety. Moreover, the remaining peaks of rlipo-D1E3 are increased by 14 amu, indicating that although there are several lipid modifications, all of them contain a double bond in their lipid moieties. These data clearly demonstrate that the lipid moieties of rlipo-D1E3 may have various lipid modifications that differ from those of Pam3.

rlipo-D1E3 Stimulates Spleen Cells to Proliferate Through TLR2

TLR2−/− and TLR4-deficient mice were used to study the effector mechanism of rlipo-D1E3. As the lipopeptides have been shown to stimulate the proliferation of spleen cells, we isolated spleen cells from wild type, TLR2−/− and TLR4-deficient mice and stimulated them with LPS (a TLR4 agonist), Pam3 (a TLR2 agonist), rlipo-D1E3 and non-lipidated E3 (rE3). We found that LPS, Pam3 and rlipo-D1E3 could stimulate the proliferation of wild type mouse-derived spleen cells, but rE3 failed to induce proliferation (FIG. 3a). The spleen cells from TLR2−/− mice did not proliferate on stimulation with Pam3 and rlipo-D1E3 (FIG. 3b). In contrast, spleen cells from TLR4-deficient mice still responded to Pam3 and rlipo-D1E3 (FIG. 3c). These results indicate that the major receptor responsible for the rlipo-D1E3-induced proliferation of spleen cells may be TLR2.

rlipo-D1E3-Induced Cytokine Production from BM-DCs is Mediated by TLR2

Figure 4:
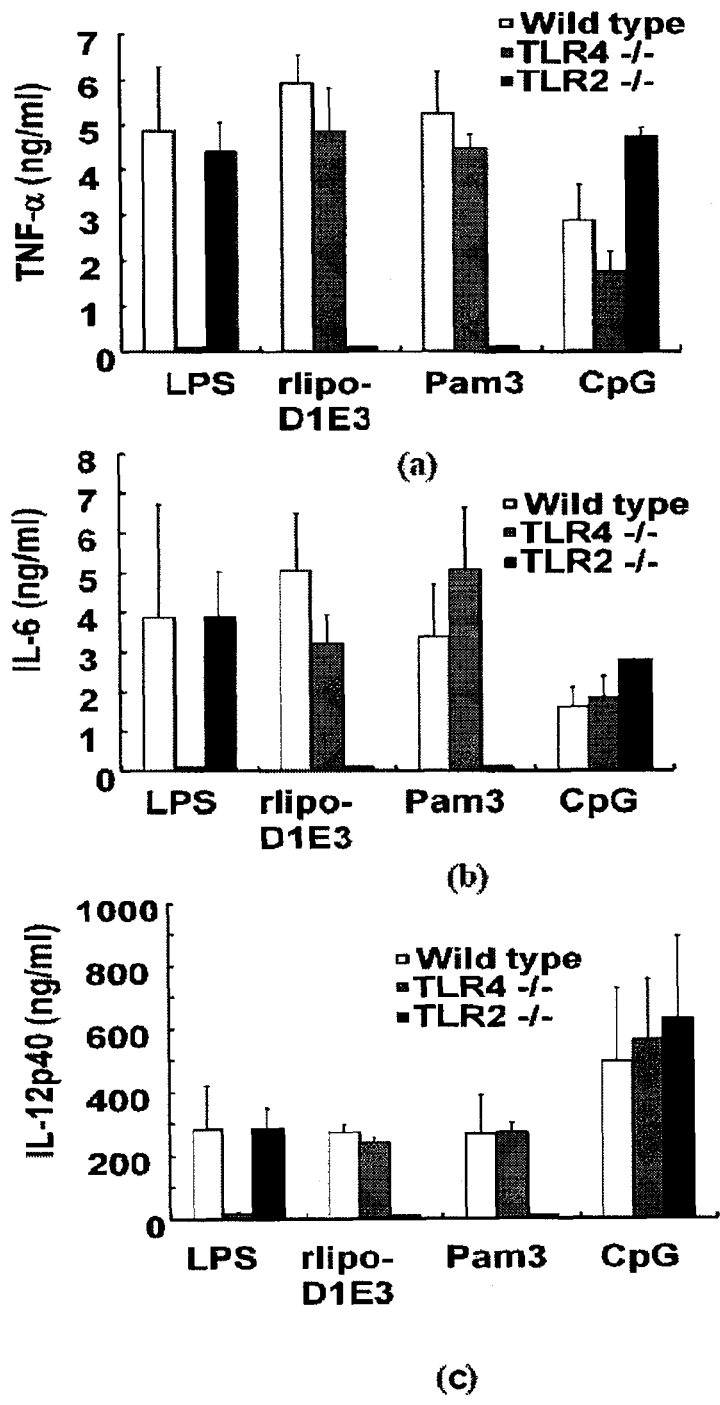
FIGS. 4a-4c are diagrams showing the effect of rlipo-D1 E3 on dendritic cells derived from wild type, TLR2-deficient and TLR4-deficient mice. The data are expressed as the mean±SD from three independent experiments. □, wild-type mice; ▒, TLR4-deficient mice; ■, TLR2-deficient mice.

BM-DCs derived from wild type, TLR2−/− and TLR4-deficient mice were used as a model to study the activation of antigen-presenting cells. As shown in FIG. 4, rlipo-D1E3 was capable of stimulating the production of TNF-α (FIG. 4a), IL-6 (FIG. 4b) and IL-12p40 (FIG. 4c) from the BM-DCs of wild type and TLR4-deficient mice, but not form the BM-DCs of TLR2−/− mice. The stimulation profile of rlipo-D1E3 was found to be similar to that obtained with the TLR2 agonist Pam3. In contrast, the stimulating effect of LPS was lost in TLR4-deficient mice, but remained in TLR2−/− and in wild type mice. Unmethylated CpGs (a TLR9 agonist), was also used as a comparison. CpG could stimulate BM-DCs to secrete cytokine release from wild type, TLR2−/− and TLR4-deficient mice (FIG. 4). These results clearly confirm that the activation of BM-DCs by rlipo-D1E3 is due to the TLR2 activating function, and not to the activation of TLR4.

rlipo-D1E3 Immunogen Activates the NF-κB Signaling Pathway Through TLR2

Figure 5:
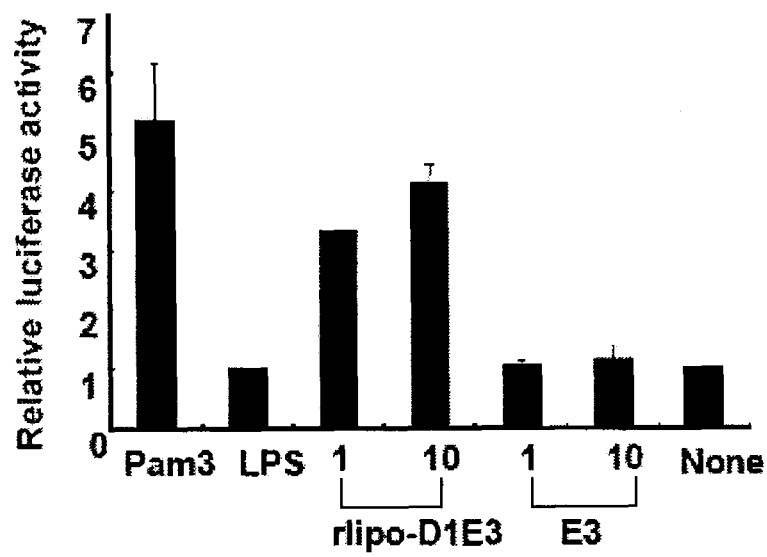
FIGS. 5a and 5b are diagrams showing induction of NF-kB signaling through TLR2. The data represent the mean±SD from triplicate samples.
Figure 5:
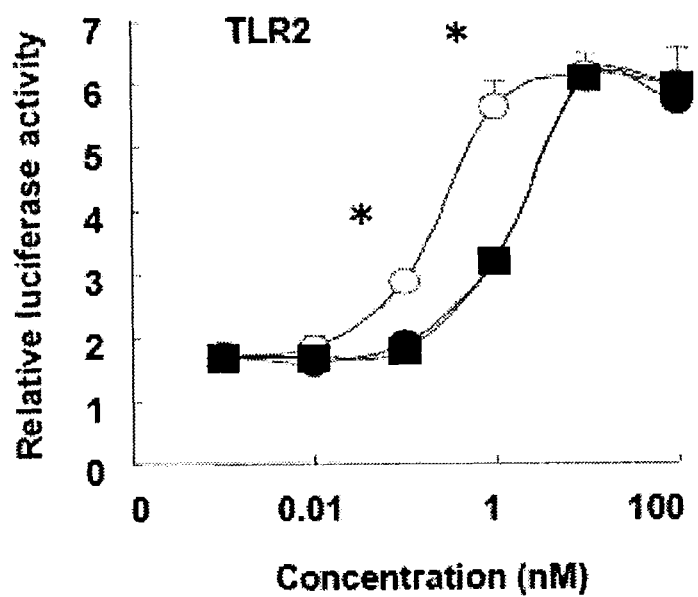

It has been shown that Pam3 triggers the NF-κB signaling pathway through human TLR2 (Morr et al. (2002) European Journal of Immunology 32, 3337-3347). In this study, we examined whether rlipo-D1 E3 could trigger the NF-κB cascade through TLR2. HEK293 cells are known to express TLR2 poorly or not at all. HEK293 cells could therefore be used for TLR2-dependent signaling assays when co-transfected with the TLR2 receptor and NF-κB reporter genes. The thymidine kinase (TK)-derived *Renilla* luciferase gene was used to normalize the transfection efficiency. As shown in FIG. 5a, stimulation of TLR2-transfected HEK293 cells by Pam3 or rlipo-D1E3 (1 and 10 nM, respectively) triggered the NF-κB signaling pathway. In contrast, stimulation with LPS and recombinant E3 (1 and 10 nM, respectively) was ineffective (FIG. 5a). Since it was suggested that the triacylated lipopeptide, Pam3, and the diacylated lipopeptide, BPP-cysPEG (a MALP-2 derivative), were recognized by different TLR2 heterodimers, TLR2/TLR1 (Takeuchi et al., (2002) J Immunol 169, $10^{-4}$.) and TLR2/TLR6 (Basinski et al. (2007) Int Arch Allergy Immunol 142, 91-8.), respectively, we performed dose-response studies to elucidate whether the signaling pathways of the TLR2-dependent responses differ depending on the TLR2 ligands used. The results demonstrated that the dose responses of rlipo-D1E3 and Pam3 are similar over the range from 1 µM to 100 nM. In contrast, BPPcysPEG exhibited a stronger activation of TLR2 (* in FIG. 5b).

rlipo-D1E3 Activates TLR Downstream Signaling in the Same Way as do Pam3 and BPPcysPEG, but with Different Kinetics In order to study the intracellular signaling pathways of antigen presenting cells after stimulation with either Pam3, rlipo-D1E3, or BPPcysPEG, the phosphorylation of p38, ERK1/2 and JNK1/2 in BM-DCs were measured at different time intervals (0, 10, 20, 40, 60, 90, and 120 min) using phosphospecific antibodies. The BPPcysPEG could induce higher level of the phosphorylation of p38, ERK1/2, JNK1/2 than Pam3 and rlipo-D1E3. This result is consistent with the NF-κB activity assay that showed BPPcysPEG could activate NF-κB in lower dose (FIGS. 5 and 6a). The highest Pam3-induced levels of the phosphorylation of p38, ERK1/2 and JNK1/2, were observed at 40 min and 120 min in BM-DCs (FIG. 6a). The highest BPPcysPEG-induced level of phosphorylation of p38, ERK1/2 and JNK1/2 was at 10 min, but this dropped down to basal levels after 60 min. In contrast, the phosphorylation level induced by rlipo-D1E3 remained at 120 min. The stimulation of antigen-presenting cells (BM-DCs) by rlipo-D1E3 could induce the same MAPK phosphorylation as do Pam3 (a TLR2/1 agonist) and BPPcysPEG (a TLR2/6 agonist), but the kinetic profiles induced by these agonists were different. Induction of phosphorylation by rlipo-D1E3 occurs earlier than with Pam3, and is sustained longer with BPPcysPEG.

rlipo-D1E3 Induces Different Cytokine and Chemokine Gene Expression in BM-DCs

Figure 7:
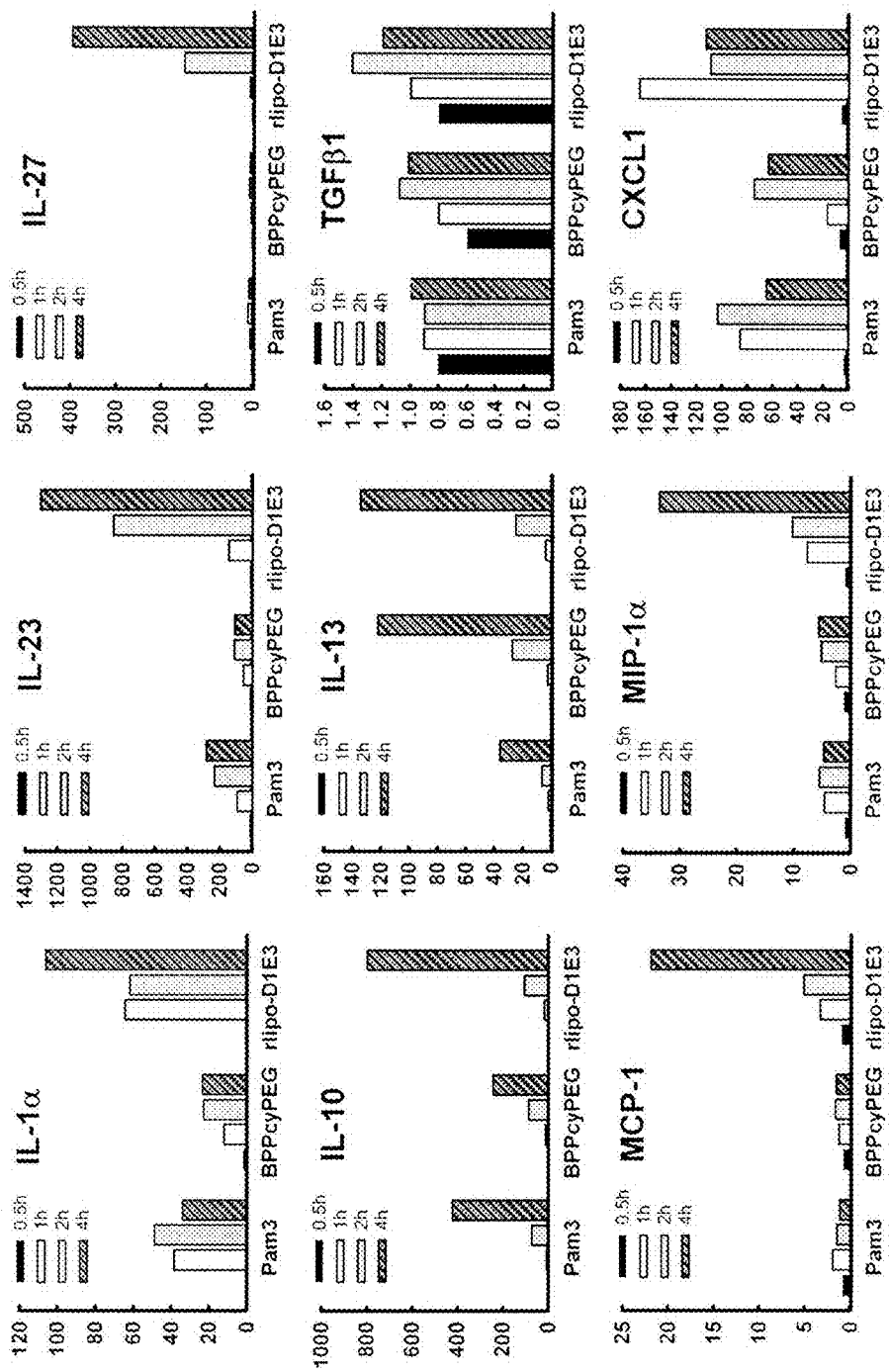
FIG. 7 is a set of diagrams showing gene expression profile of cytokines or chemokines in murine BM-DCs. The data shown are representative of two independent experiments.
Figure 8:
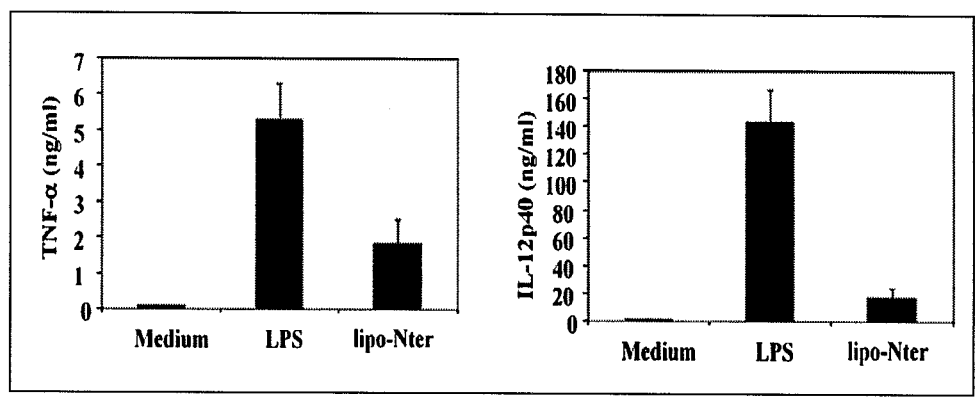
FIG. 8 is a set of diagrams showing that lipo-Nter can stimulate bone marrow-derived dendritic cells to secrete TNF-α and IL-12p40.
Figure 9:
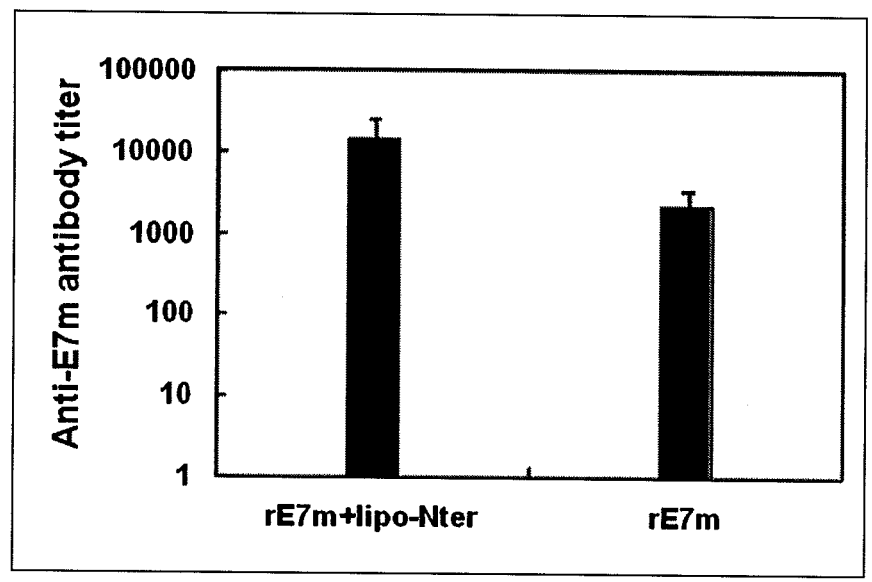
FIG. 9 is a diagram showing that lipo-Nter combined with recombinant mutant E7 (rE7m) can enhance anti-E7 antibody.
Figure 10:
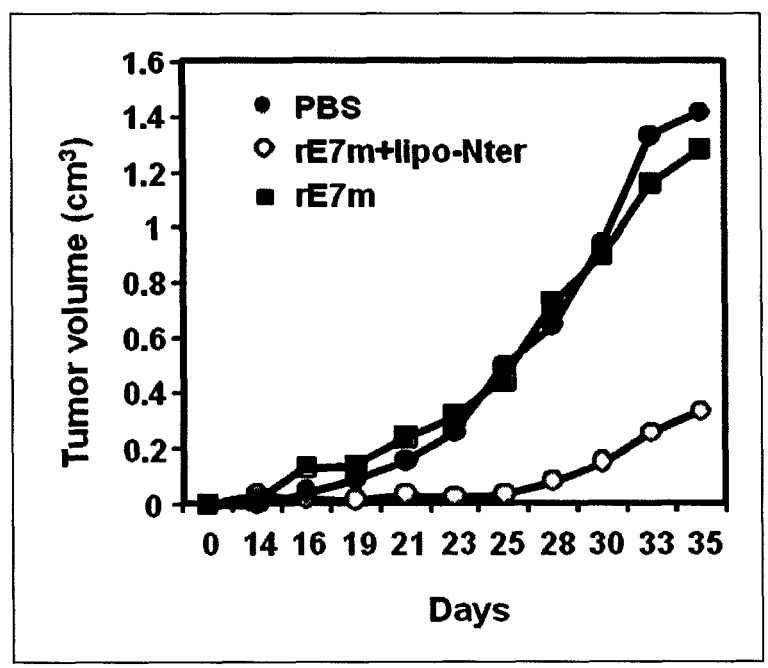
FIG. 10 is a diagram showing that lipo-Nter combined with rE7m can increase the tumor growth inhibition ability.
Figure 11:
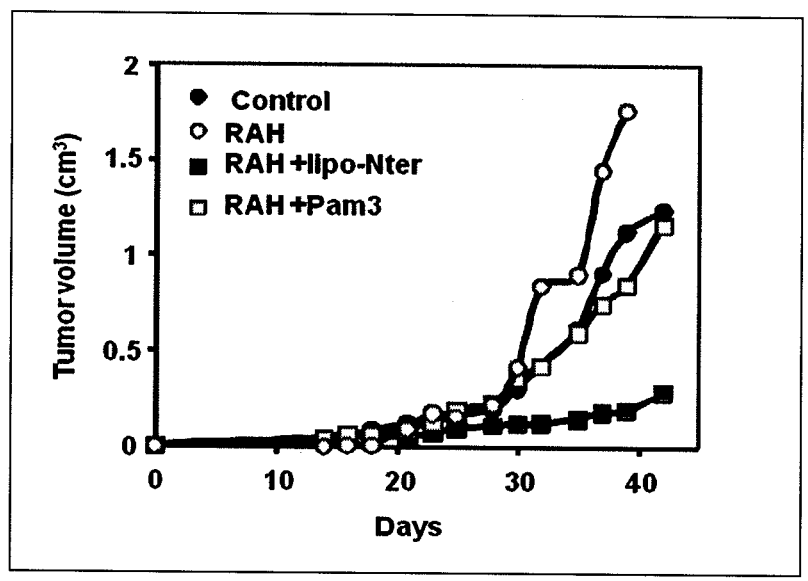
FIG. 11 is a diagram showing that lipo-Nter combined with rE7m can increase the tumor growth inhibition ability, but the synthetic lipopeptide Pam3 cannot Inhibit tumor growth.

In order to elaborate whether rlipo-D1E3 elicits different downstream gene expression than Pam3 and BPPcysPEG, we examined the gene expression profile of cytokines and chemokines in BM-DCs after stimulation with Pam3, BPPcysPEG or rlipo-D1E3. The gene expression of the control group (medium alone) was set as 1 when normalizing the gene expression levels after stimulation. rlipo-D1E3 induced higher expression levels of IL-1α, IL-23, IL-27, MCP-1 and MIP-1α. rlipo-D1E3 and BPPcysPEG induced higher expression levels of IL-13 compared to Pam3. In contrast, IL-10, TGFβ and CXCL1 expression levels were similar after Pam3, BPPcysPEG or rlipo-D1E3 stimulation (FIG. 7). These results suggest that while rlipo-D1E3, Pam3 and BPPcysPEG activate BM-DCs through the same receptor (TLR2), and a similar MAPK signaling pathway. However, they may induce different gene expression levels.

Most native bacterial lipoproteins activate innate immune responses through the TLR2/1 or TLR2/6 heterodimeric receptors that are present on antigen-presenting cells. However, the recombinant lipoprotein OprI from *Pseudomonas aeruginosa* when expressed in *E. coli* was shown to stimulate dendritic cells through TLR2/4 ligation. These controversial results led us to analyze the lipid structures and the effector mechanisms of a recombinant dengue virus vaccine, rlipo-D1E3, that exhibits intrinsic adjuvant properties, specifically because the information on the structure of lipid moieties in bacterial derived lipoproteins are very limited. Recently, the lipid moiety of a 30-35 kDa lipoprotein derived from *Staphylococcus aureus* that stimulates cells through TLR2 was identified as a diacylated protein by tandem mass (MS/MS) spectrometry. Post-translational lipid modifications in lipoproteins vary among bacteria. The lipidation signal sequence that we used to engineer the rlipo-D1E3 immunogen is derived from *Neisseria meningiditis*, and the lipoprotein was over-expressed in *E. coli*. The lipo-immunogen was shown to have strong intrinsic adjuvant activity. We were therefore interested in establishing the specificity of the TLRs and the underlying intracellular signaling mechanisms that are responsible for the immunomodulatory activity of rlipo-D1E3. We have shown that rlipo-D1E3 is triacylated with unsaturated fatty acids. Three tryptic peptide peaks can be observed using MS/MS following liquid-phase tryptic digestion of rlipo-D1E3. However, after purifying the tryptic fragments of rlipo-D1E3, five lipid modifications were observed, and each modification corresponds to a 14 amu difference in atomic mass (FIGS. 2c, d, e, and f). These data suggest that the fatty acids of rlipo-D1 E3 exist as lipid moieties containing different numbers of methylene (CH2) groups. From our results, we estimated that one of the fatty acids from rlipo-D1 E3 may be unsaturated (one double bond). This type of lipid modification may result in different effector mechanisms for activating innate immunity.

Figure 3:
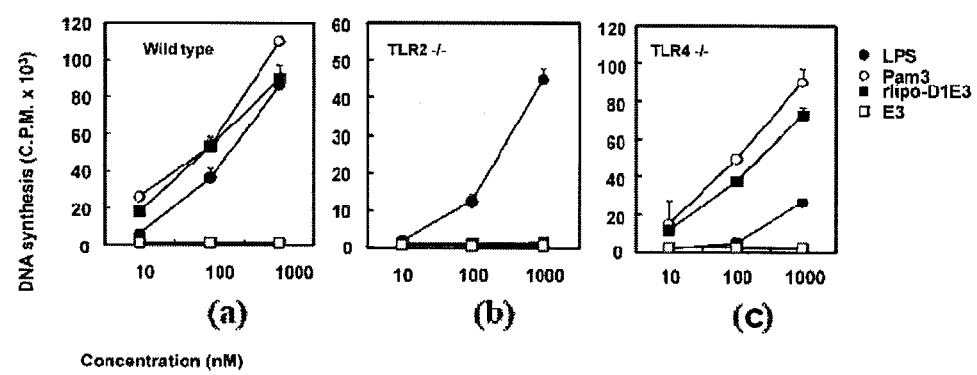
FIGS. 3a-3b are diagrams showing DNA synthesis in splenocytes from TLR2−/−, TLR4-deficient and wild-type mice after stimulation with rlipo-D1E3. The data represent the mean±SD of triplicate samples.

To understand the effector stimulation mechanisms, we have studied the binding specificity of the receptors and the intracellular signaling of rlipo-D1E3. We found that rlipo-D1E3 did not have any effect on TLR2-deficient mice, while retaining stimulatory activity for cells from wild type and TLR4-deficient mice (FIG. 3 and FIG. 4). These data demonstrated that the major receptor used by rlipo-D1E3 is TLR2, but not TLR4. These results differ from those from a previous report on recombinant OprI, which uses TLR2/4. This might be due to the differences in the lipid composition of the two lipoproteins or due to different production methods. Therefore, the recombinant lipoprotein activate TLR2 may have different effects with other TLR2 agonists on APC. Although it was found that the heterodimerization of TLR2 with TLR1 or TLR6 does not lead to differential intracellular signaling, we interested to investigate whether the recombinant lipoprotein rlipo-D1E3 showed different intracellular signaling. In NF-κB reporter assay, the Pam3, rlipo-D1E3 and BPPcysPEG could induce signal transduction through NF-kB pathway. However, at 0.1 or 1 nM concentration, the BPPcysPEG induce highest NF-κB signaling activities (FIG. 5b). Furthermore, we found here that stimulation with either rlipo-D1E3, Pam3, or BPPcysPEG on BM-DCs induced similar pattern of phosphorylation on p38, ERK1/2, and JNK1/2 in BM-DCs (FIG. 6a), but the phosphorylation level of p38, ERK1/2 and JNK1/2 induced by BPPcysPEG was stronger and earlier than that of Pam3 or rlipo-D1E3. Interestingly, we noted that rlipo-D1E3 looks have a prolonged signaling of p38 phosphorylation (FIG. 6b). We did not know whether the prolonged signaling have any impact on activation of antigen-presenting cells. Therefore, we used the same amount of the Pam3, BPPcysPEG and rlipo-D1E3 to stimulate BMDCs, we found that rlipo-D1E3 induces higher levels of inflammatory cytokine and chemokine RNA transcripts (IL-1α, IL-23, IL-27, MCP-1, MIP-1α) (FIG. 7). The up-regulation of cytokines and chemokines after stimulation with rlipo-D1E3 indicated the recombinant lipoprotein may have different effector function compare to other TLR2 agonists (Pam3 or BPPcysPEG). Moreover, Farhat et al. used either FSL-1 (TLR1-dependent), Pam2C-SK4 (TLR1- and TLR6-dependent), or PamOct2C0 (VPGVG)-4VPGKG (SEQ ID NO.: 13) (TLR6-dependent) to stimulate murine dendritic cells, and analyzed the phosphorylation of MAPK and the gene expression profiles. They concluded that the lipoproteins that are present in different pathogens might activate different TLR dimers, but use the same signaling cascade for gene activation (J Leukoc Biol 83, 692-701.). We wonder whether the unique double bond of lipid moiety or the D1E3 domain of rlipo-D1E3 contributed the induction of higher level of cytokine and chemokine genes expression. Currently, we are trying to isolate and purify the N-terminal lipid moiety of rlipo-D1E3 for further studies. Taken together, the elevated expression levels of cytokines and chemokines imply that the effector mechanisms of rlipo-D1E3 are different from that of Pam3 or BPPcysPEG. Its N-terminal lipid moiety could be used as novel adjuvants to modulate immune responses for future vaccine development.

Example 2

In this example, assays were conducted for digestion of rlipo-D1E3 and purification of lipidated N-terminal fragments (lipo-Nter). Briefly, 100 mg of purified rlipo-D1E3 were digested with typsin by a ratio of 50:1 at room temperature for 4 hours. Then, the reaction mixture was stopped by adding 100% formic acid to a ratio of 100:3. Then, 7.2 g of C18 silica gel (Fluka (Buchs, Switzerland), reversed phase silica gel 100 C18) was dissolved in 200 ml of 100% acetonitrile (CAN) and pre-equilibrated with 80 ml of 0.1% Trifluoroacetic acid (TFA). After that, 100 mg of digested rlipo-D1 E3 were loaded into C18 column. The column was washed with 200 ml of 0.1% TFA and was further washed with 400 ml of 70% ACN/0.1% TFA. The final washing was performed by using 120 ml of 100% ACN. The lipidated N-terminal fragments was then eluted by using 40 ml of isopropanol and subject to MALDI-TOF mass spectrum.

Figure 1B:
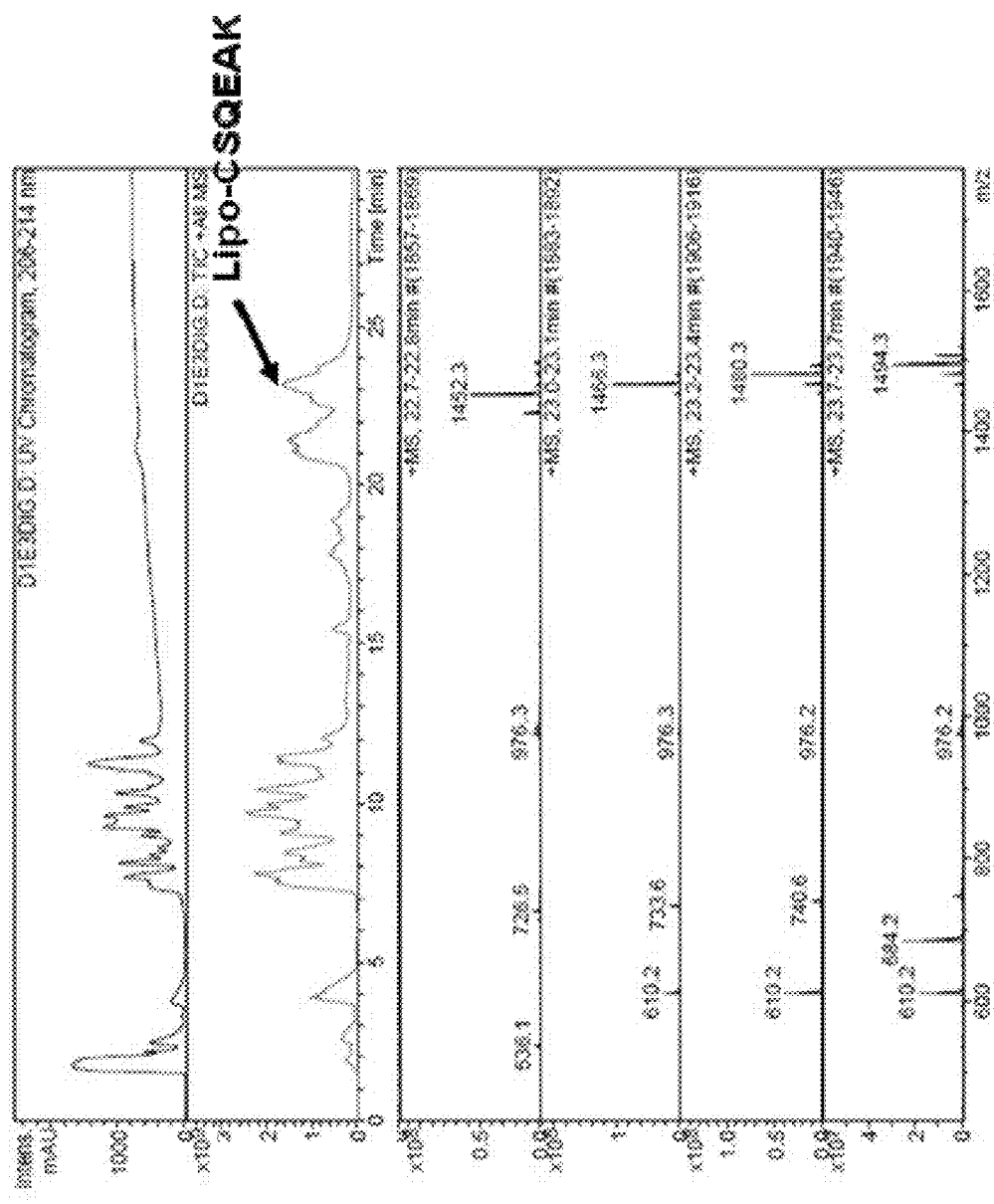
Figure 2:
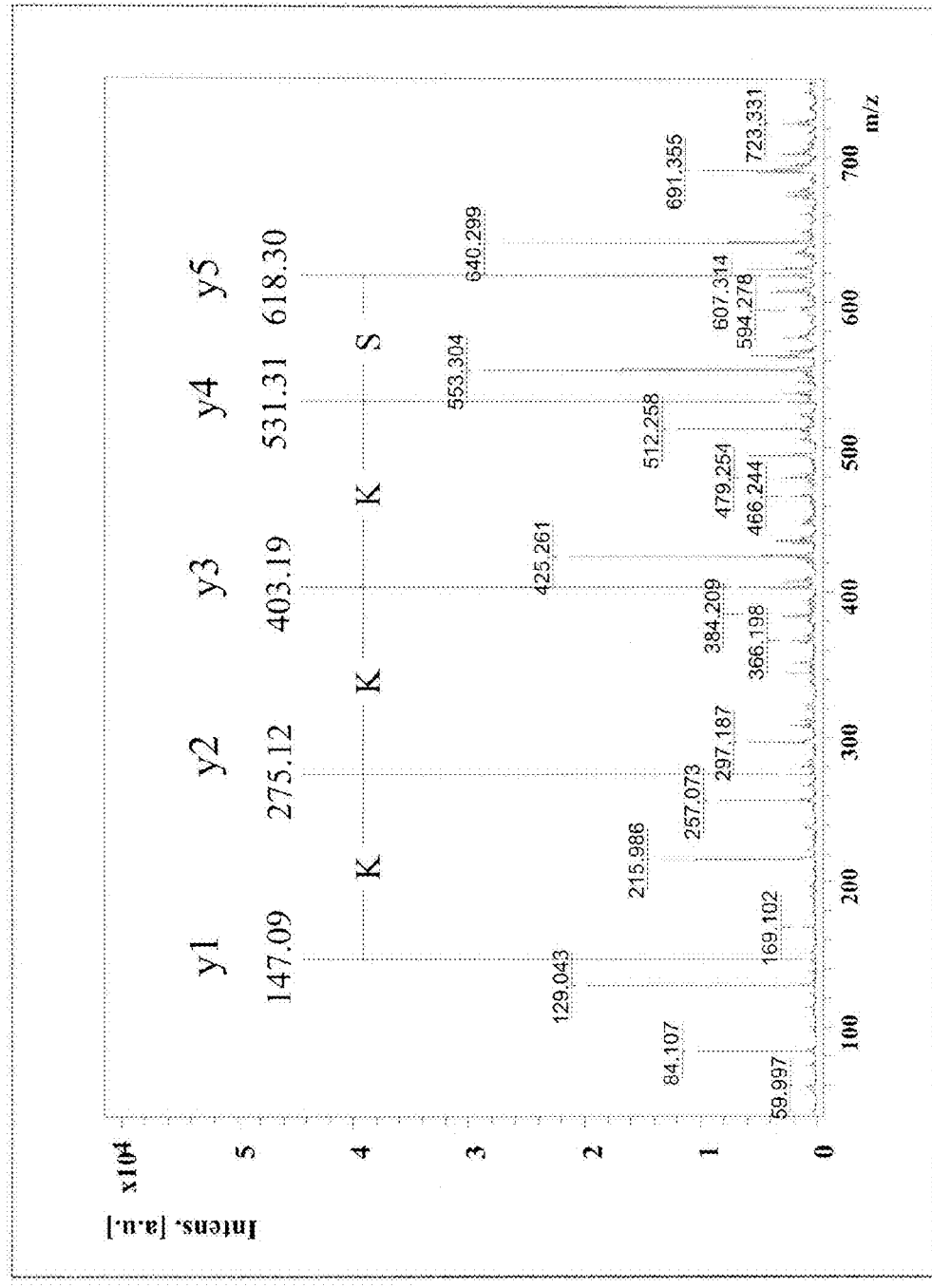
FIGS. 2a-f are diagrams showing identification of the synthetic lipo-peptide and purified N-terminal fragments of rlipo-D1E3.
Figure 2:
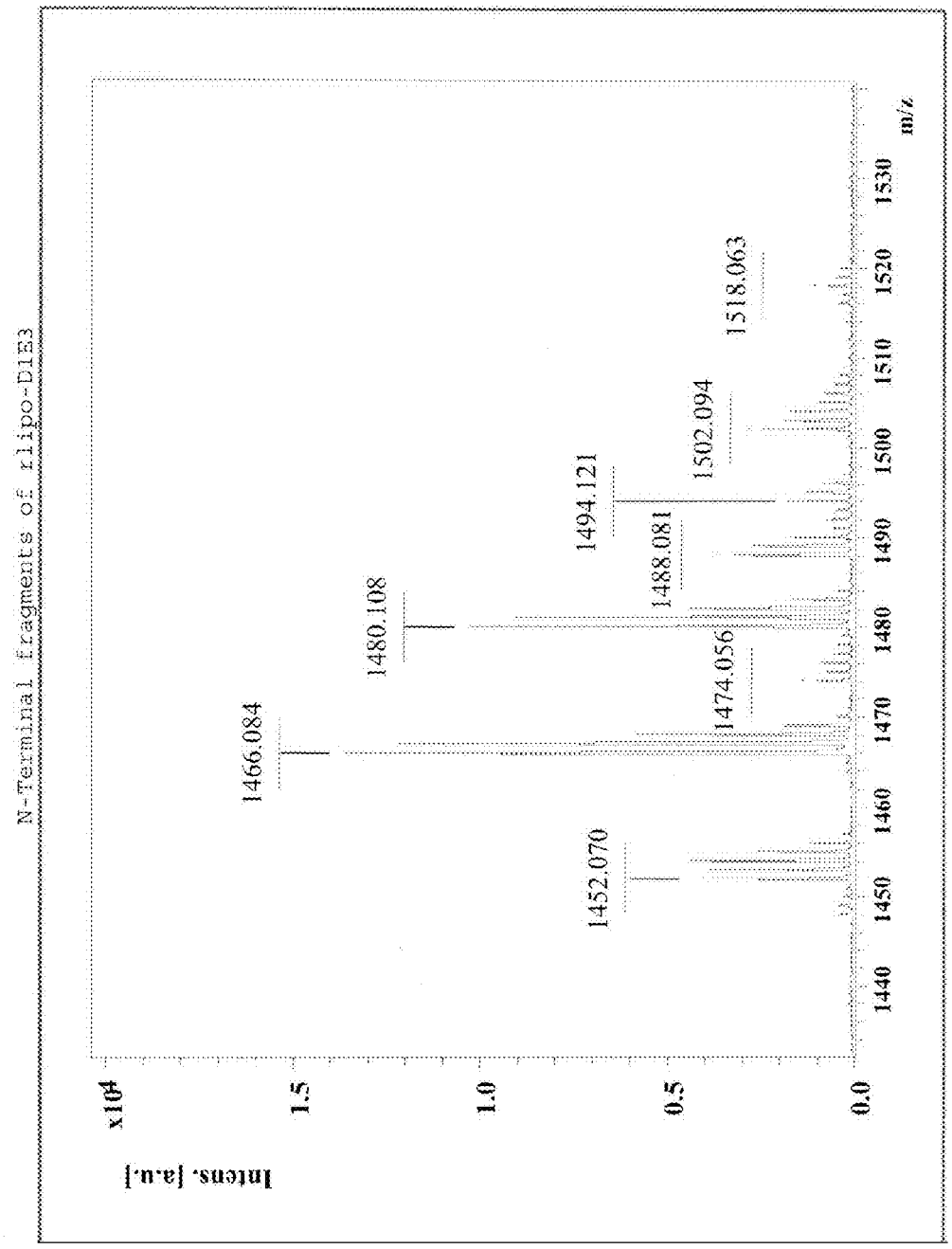
Figure 2C:
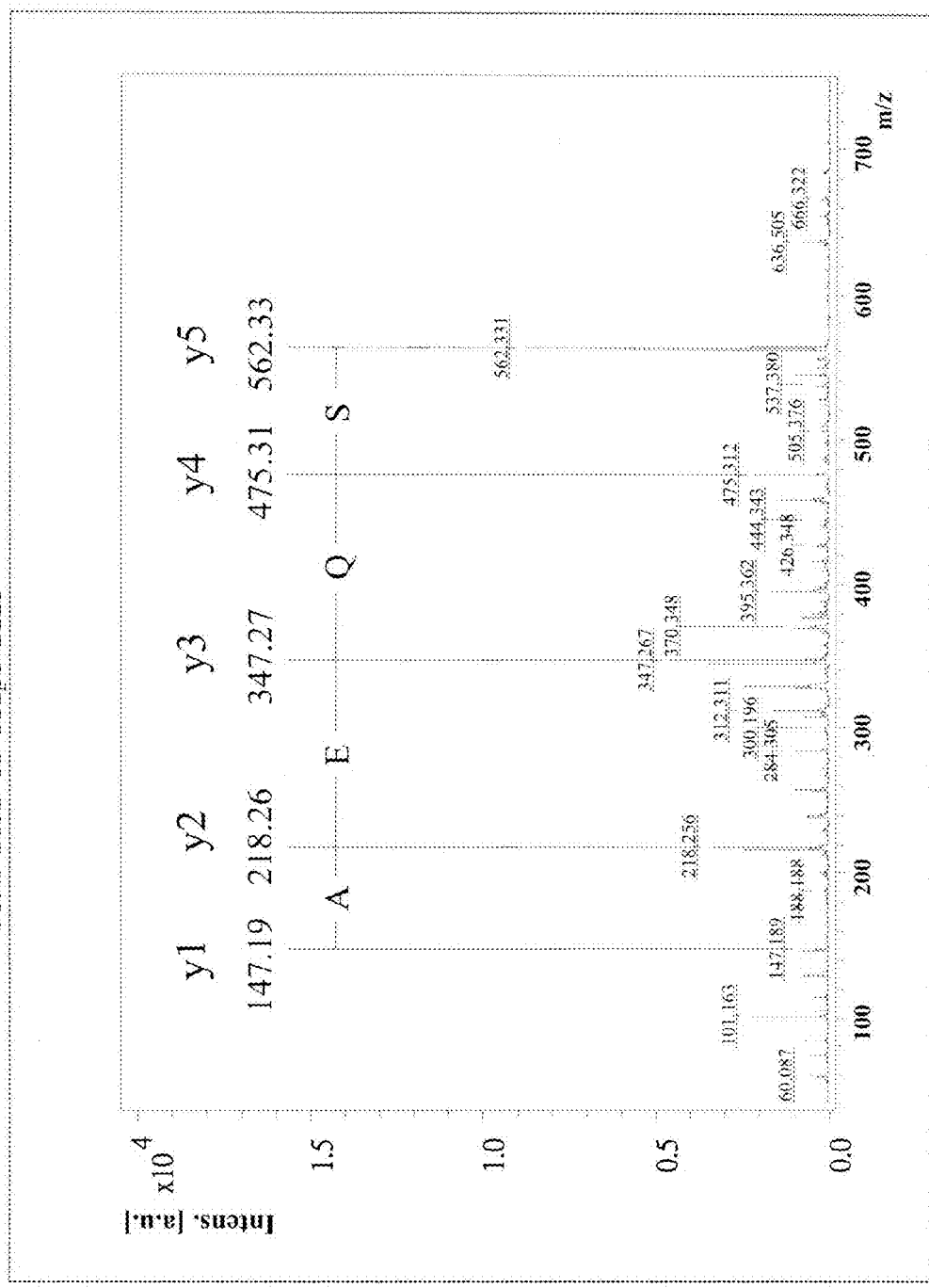
Figure 2:
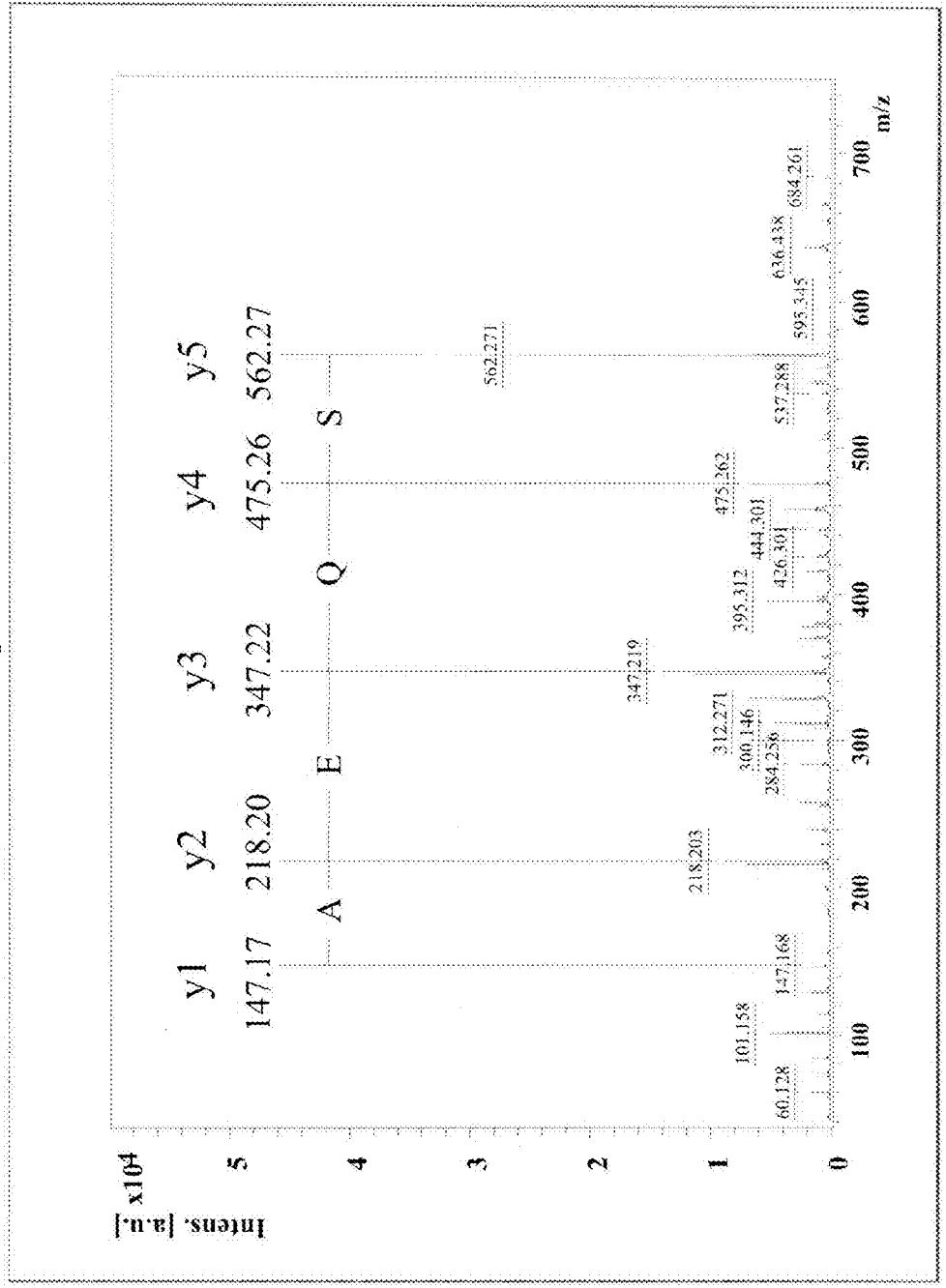

The results are shown in FIGS. 1 and 2. As shown in the figures, the MALDI-TOF mass spectrum results indicated that the molecular ion mass (m/z) matched that of predict N-acyl-S-diacylglyceryl-CSQEAK (SEQ ID NO.: 11). The molecular ion mass 1452, 1466, 1480 and 1494 imply that fatty acids at position R1 (or at R2), are of the same number of carbon (C16:0), or the same mixture of (C16:1), (C17:1) and (C18:1), and that B), the neutral lose of the unsaturated fatty acid is from the same R1 or R2 position.

Figure 2E:
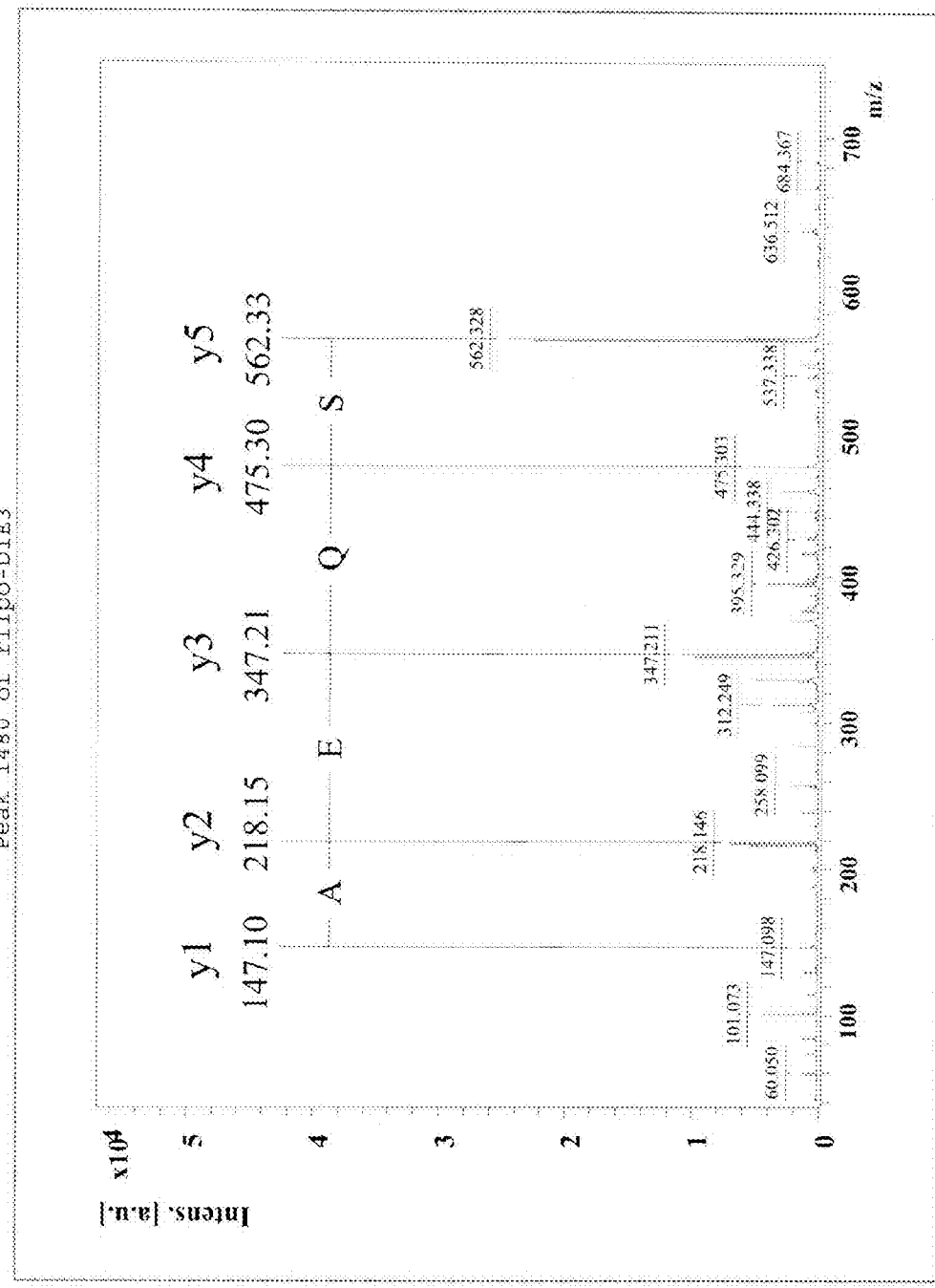
Figure 2:
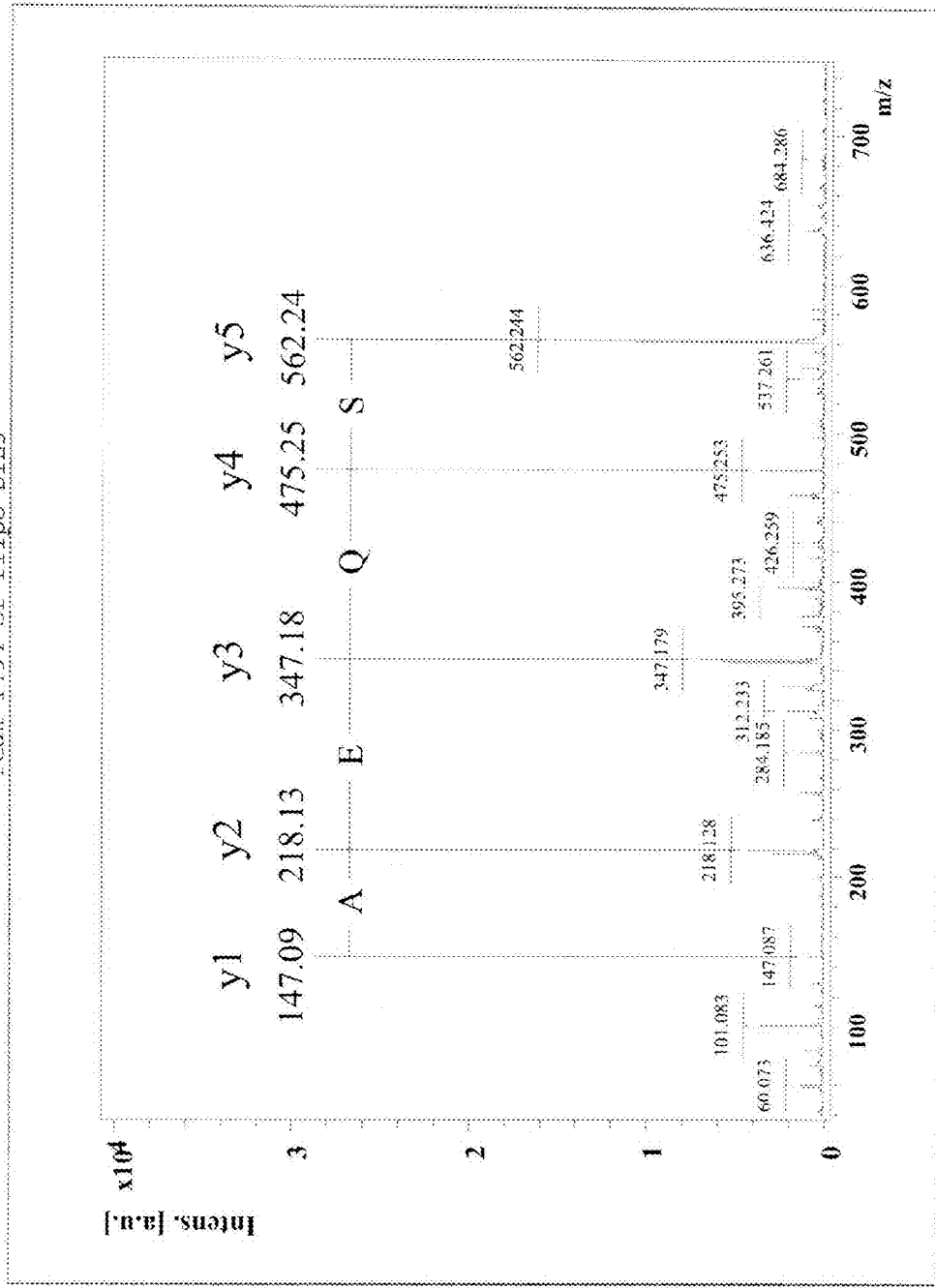

As shown in FIG. 2a, the molecular mass of Pam3 is 1509.6 daltons and the sequence is lipid-Cys-Ser-Lys-Lys-Lys-Lys (SEQ ID NO.: 14). The y-ions of y1-y5 have been identified, and they confirm that the sequence has no further modifications. The mass of N-acyl-S-diacylglyceryl-cysteinyl from Pam3 is 892.2, which agrees with the expected composition: SNO6C54H102. As shown in FIG. 2b, there are five major peaks that can be identified in the mass spectrum of rlipo-D1E3. As shown in FIG. 2c, the y-ions of y1-y5 have been identified, and they confirm that the sequence has no further modifications. The mass of N-acyl-S-diacylglyceryl-cysteinyl of peak 1452.2 is 890.0. As shown in FIG. 2d, the y-ions of y1-y5 have been identified, and they confirm that the sequence has no further modifications. The mass of N-acyl-S-diacylglyceryl-cysteinyl of peak 1466.2 is 904.0. As shown in FIG. 2e, the y-ions of y1-y5 have been identified, confirming that the sequence has no further modifications. The mass of N-acyl-S-diacylglyceryl-cysteinyl of peak 1480.2 is 918.0. As shown in FIG. 2f, the y-ions of y1-y5 have been identified, confirming that the sequence has no further modifications. The mass of N-acyl-S-diacylglyceryl-cysteinyl of peak 1494.2 is 932.0.

Example 3

This example describes separation of lipidated N-terminal fragments (lipo-Nter). The above-described tryptic digested rlipo-D1E3 were firstly added into, mixed and incubated with 50 uL of POROS resin (Applied Biosystems, CA), which was pre-wetted with (100%) of acetonitrile, for at least 2 hours. The POROS resin mixture was loaded on to a 0.6 mL Eppendorf tube with a small opening at the bottom created by inserting a 22 gauge needle, was placed on top of a 1.5 mL Eppendorf tube. The wasted liquid was filtered and collected by quick centrifugation using a table-top microfuge. The POROS resin was washed with (0.2 mL 3 to 5 times) of 0.1% TFA water, then eluted first with 0.05 mL of 100% acetonitrile and followed with 0.05 mL of 100% isopropanol. The lipo-Nter with molecular ion mass (m/z) matched that of predict N-acyl-5-diacylglyceryl-CSQEAK (SEQ ID NO.: 11) were found in the sequential elution of 100% isopropanol.

The results are shown in FIG. 3. As shown in the figure, the lipo-Nter were actually separated and eluted out at different time according the mass, even with 14 amu difference.

Example 4

In this example, assays were conducted to examiner whether the lipo-Nter can stimulate bone marrow-derived dendritic cells to secrete TNF-α and IL-12p40.

BM-DCs were harvested as previously described (Lutz et al., 1999). Briefly, femurs and tibiae of 6-8 week old female mice were removed, and the bone marrow cells were dispersed by vigorous pipetting. After removing red blood cells with lysis buffer, the isolated bone marrow cells were resuspended to a density of $2-5 \times 10^5$/ml cells with RPMI-10: RPMI-1640 (GIBCO BRL, Grand Island, N.Y.) supplemented with 10% P/S, L-glutamine (2 mM, Sigma), 2-mercaptoethanol (50 μM, Sigma), and 10% heat-inactivated FBS. On days 0, 3, and 6, bone marrow cells were added to Petri dishes containing 200 U/mL (20 ng/ml) of recombinant mouse granulocyte macrophage colony stimulating factor (MoGM-CSF, Peprotech, Rocky Hill, N.J.) in RPMI-10. At day 6, either LPS (0.01 μg/ml), lipo-Nter (100 nM) was added. Generally, immature dendritic cells made up 70% of the total cell population.

The production of cytokines by BM-DCs was determined using ELISA. Briefly, 100 μL of anti-cytokine (10 μg/ml of IL-12p40, TNF-α) antibodies (R&D system Inc. Minneapolis, Minn.) were coated onto 96-well microtiter plates with 0.1 M carbonate buffer, pH 9.6, following overnight incubation at 4° C. The coated plates were washed twice with 0.05% Tween 20 in PBS and then blocked with 5% non-fat milk in PBS at room temperature for 2 hours. Diluted supernatants from stimulated BM-DCs were applied to the coated wells at room temperature for 2 hours. Following the addition of biotin-conjugated, anti-cytokine antibodies (R&D system Inc. Minneapolis, Minn.), the assay was developed with 3,3',5,5'-tetramethylbenzidine (TMB), and the reaction was stopped by adding 100 μl of 1 M $H_2SO_4$ per well. The plates were read at 450 nm using an ELISA plate reader (Molecular Devices, CA). The production levels of the cytokines were calculated by subtracting the values obtained for non-stimulated groups.

As shown in FIG. 4. the results indicated that lipo-Nter stimulated bone marrow-derived dendritic cells to secrete TNF-α and IL-12p40.

Example 5

In this example, assays were conducted to examiner whether the lipo-Nter combined with recombinant mutant E7 (rE7m) can enhance anti-E7 antibody.

Five mice (6-8 weeks old) were immunized subcutaneously with 20 μg of rE7m with or without lipo-Nter. The mice were given two immunizations at two-week intervals. Blood was collected from each mouse at different time points as indicated. Sera were prepared and stored at −80° C. until use. The level of anti-E7m IgG in the serum samples was determined by titrating the samples in 96-well plates coated with purified rE7m. Bound IgG was detected with horseradish peroxidase-conjugated goat anti-mouse IgG Fc. After the addition of TMB, the absorbance was measured with an ELISA reader at 450 nm. As shown in FIG. 5, the results indicated that lipo-Nter combined with recombinant mutant E7 (rE7m) enhanced anti-E7 antibody.

Example 6

Figure 6:
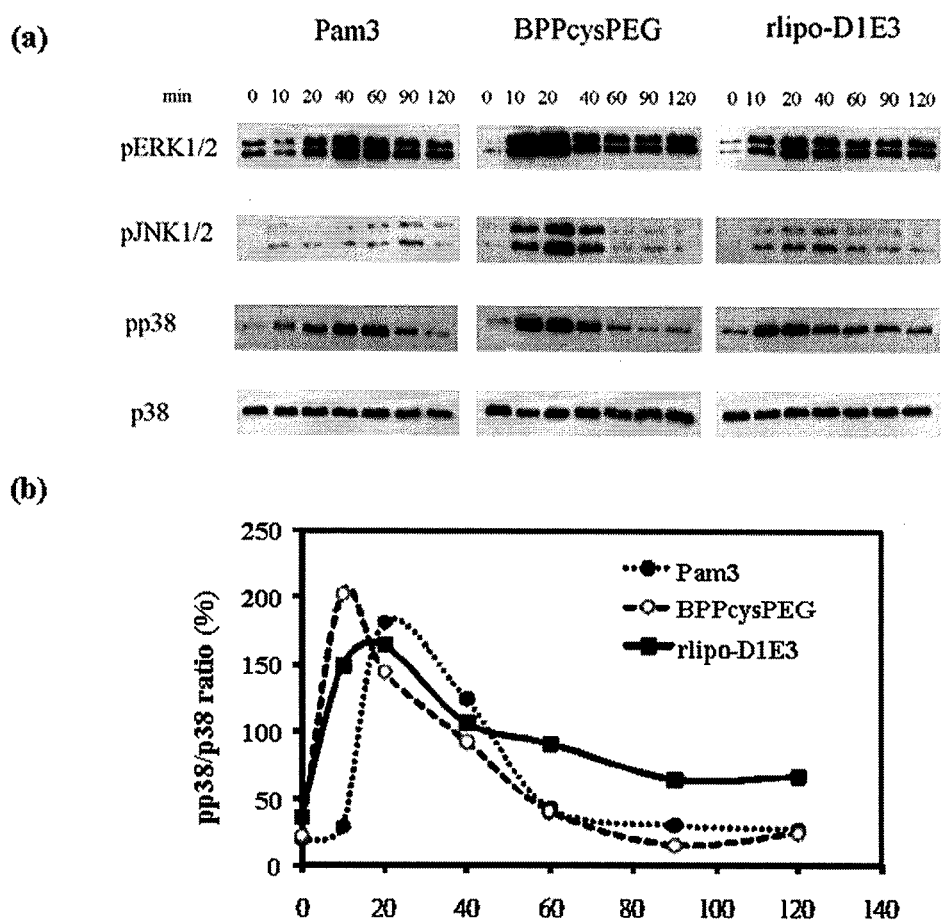
FIGS. 6a and 6b are diagrams showing activation of p38, ERK1/2, JNK1/2 in murine bone marrow-derived dendritic cells (BM-DCs).

In this example, assays were conducted to examiner whether the lipo-Nter combined with rE7m can increase the tumor growth inhibition ability. Six mice (6-8 weeks old) were inoculated with 2×10$^5$ TC-1 cells (expressed HPVE7 cells) at day 0. After 7 days, mice were immunized once subcutaneously with 20 μg of rE7m with or without lipo-Nter. The tumor size was monitored every 2-3 days until tumor volumes higher than 3000 mm$^3$. The tumor volumes were calculated based on the formula length×width×width/2. As shown in FIG. 6, the results indicated that rE7m could induce anti-tumor effect in the presence of lipo-Nter. In other words, rE7m and lipo-Nter, in combination, unexpectedly has an anti-tumor activity stronger than that of rE7m alone.

Example 7

In this example, assays were conducted to examine whether the lipo-Nter combined with E7-derived CTL epitope peptide RAHYNIVTF ("RAH") can increase the tumor growth inhibition ability, but not the synthetic lipopeptide Pam3.

Six mice (6-8 weeks old) were inoculated with 2×10$^5$ TC-1 cells (expressed HPVE7 cells) at day 0. After 7 days, mice were immunized once subcutaneously with 20 μg of E7-derived peptide in the presence of tripamitoylated peptide Pam3 or lipo-Nter. The tumor size was monitored every 2-3 days until tumor volumes higher than 3000 mm$^3$. The tumor volumes were calculated based on the formula length×width× width/2. The results indicated that the lipo-Nter enhanced anti-tumor effect of synthetic peptide-based immunotherapy.

Furthermore, it was found that E7-drived peptide RAH combined with lipo-Nter could inhibit tumor growth in mice. In contrast, the combination RAH with synthetic lipopeptide Pam3 failed to inhibit tumor growth. See FIG. 7.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated lipopeptide, wherein the lipopeptide is N-acyl-S-diacylglyceryl-CSQEAK (SEQ ID NO:11) or N-acyl-S-diacylglyceryl-CSQEAKQEVK (SEQ ID NO:10).

2. The isolated lipopeptide of claim 1, wherein the lipopeptide is

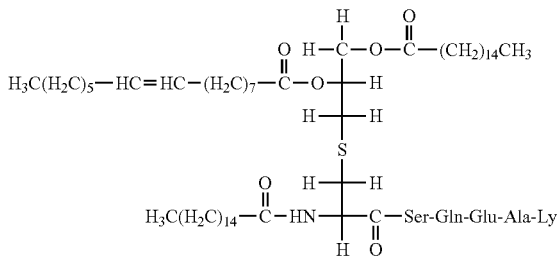
(SEQ ID NO: 7)

3. The isolated lipopeptide of claim 1, wherein the lipopeptide is N-acyl-S-diacylglyceryl-CSQEAK (SEQ ID NO:11).

4. The isolated lipopeptide of claim 1, wherein the lipopeptide is N-acyl-S-diacylglyceryl-CSQEAKQEVK (SEQ ID NO:10).

5. An adjuvant composition comprising the isolated lipopeptide of claim 1.

6. The adjuvant composition of claim 5, wherein the isolated lipopeptide of claim 1 is (SEQ ID NO: 7)

7. An immunogenic composition comprising an antigen and the isolated lipopeptide of claim 1.

8. The immunogenic composition of claim 7, wherein the isolated lipopeptide of claim 1 is

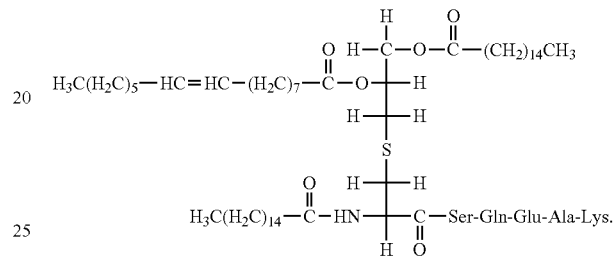
(SEQ ID NO: 7)

9. A method of inducing an immunological response in a subject comprising administering to a subject in need thereof an antigen and the isolated lipopeptide of claim 1.

10. The method of claim 9, wherein the isolated lipopeptide of claim 1 is

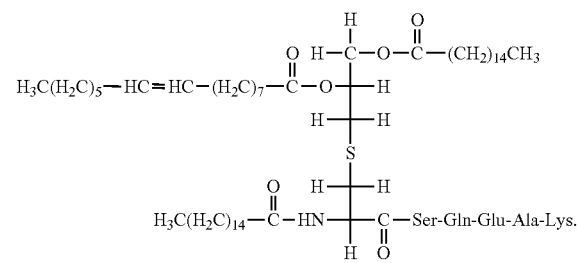
(SEQ ID NO: 7)

11. A method of preparing the isolated lipopeptide of claim 1, comprising:
   providing a host E. coli cell containing a nucleic acid encoding a protein that has the sequence of SEQ ID NO: 1, 6, or 9 at the N-terminus;
   cultivating the host E. coli cell in a medium under condition permitting expression of the protein in lipidated form as set forth in claim 1;
   purifying the lipidated form of the protein from the cell or the medium;
   digesting the lipidated form of the protein with a protease to generate the lipopeptide of claim 1; and
   isolating the lipopeptide of claim 1.

12. The method of claim 11, wherein the nucleic acid is heterologous to the E. coli host cell.

13. The method of claim 11, wherein the protein has includes the sequence of SEQ ID NO: 1, or 9 at the N-terminus.

14. The method of claim 11, wherein the isolated lipopeptide of claim 1 is
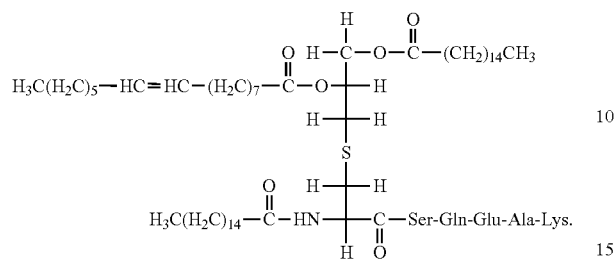
(SEQ ID NO: 7)
* * * * *

SEQUENCE LISTING

```
<160> NUMBER OF SEQ ID NOS: 35

<210> SEQ ID NO 1
<211> LENGTH: 121
<212> TYPE: PRT
<213> ORGANISM: Neisseria meningitidis

<400> SEQUENCE: 1

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp
    50                  55                  60

Ala Lys Ala Ser Ala Glu Glu Ala Val Thr Glu Ala Lys Glu Ala Val
65                  70                  75                  80

Thr Glu Ala Lys Glu Ala Val Thr Glu Ala Lys Glu Ala Val Thr Glu
                85                  90                  95

Ala Ala Lys Asp Thr Leu Asn Lys Ala Ala Asp Ala Thr Gln Glu Ala
            100                 105                 110

Ala Asp Lys Met Lys Asp Ala Ala Lys
        115                 120
```

```
              115                 120

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 1-17 of Ag473

<400> SEQUENCE: 2

Met Lys Lys Leu Leu Ile Ala Ala Met Met Ala Ala Leu Ala Ala
1               5                   10                  15

Cys

<210> SEQ ID NO 3
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 18-40 of Ag473

<400> SEQUENCE: 3

Ser Gln Glu Ala Lys Gln Glu Val Lys Glu Ala Val Gln Ala Val Glu
1               5                   10                  15

Ser Asp Val Lys Asp Thr Ala
            20

<210> SEQ ID NO 4
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 41-71 of Ag473

<400> SEQUENCE: 4

Ala Ser Ala Ala Glu Ser Ala Ala Ser Ala Val Glu Glu Ala Lys Asp
1               5                   10                  15

Gln Val Lys Asp Ala Ala Ala Asp Ala Lys Ala Ser Ala Glu Glu
            20                  25                  30

<210> SEQ ID NO 5
<211> LENGTH: 50
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 72-121 of Ag473

<400> SEQUENCE: 5

Ala Val Thr Glu Ala Lys Glu Ala Val Thr Glu Ala Lys Glu Ala Val
1               5                   10                  15

Thr Glu Ala Lys Glu Ala Val Thr Glu Ala Ala Lys Asp Thr Leu Asn
            20                  25                  30

Lys Ala Ala Asp Ala Thr Gln Glu Ala Ala Asp Lys Met Lys Asp Ala
        35                  40                  45
```

Ala Lys
    50

<210> SEQ ID NO 6
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 1-40 of Ag473

<400> SEQUENCE: 6

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala
        35                  40

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 18-22 of Ag473

<400> SEQUENCE: 7

Ser Gln Glu Ala Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 18-26 of Ag473

<400> SEQUENCE: 8

Ser Gln Glu Ala Lys Gln Glu Val Lys
1               5

<210> SEQ ID NO 9
<211> LENGTH: 71
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 1-71 of Ag473

<400> SEQUENCE: 9

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Ala Ser Ala Ala Glu Ser Ala Ala
        35                  40                  45

Ser Ala Val Glu Glu Ala Lys Asp Gln Val Lys Asp Ala Ala Ala Asp

```
                 50                  55                  60

Ala Lys Ala Ser Ala Glu Glu
 65                  70

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 17-26 of Ag473

<400> SEQUENCE: 10

Cys Ser Gln Glu Ala Lys Gln Glu Val Lys
 1               5                  10

<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid residues 17-22 of Ag473

<400> SEQUENCE: 11

Cys Ser Gln Glu Ala Lys
 1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 12

Ser Lys Lys Lys Lys
 1               5

<210> SEQ ID NO 13
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 13

Val Pro Gly Val Gly
 1               5

<210> SEQ ID NO 14
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 14

Cys Ser Lys Lys Lys Lys
 1               5

<210> SEQ ID NO 15
<211> LENGTH: 9
<212> TYPE: PRT
```

-continued

```
<213> ORGANISM: Artificial sequence
<220> FEATURE:
<223> OTHER INFORMATION: Synthetic polypeptide

<400> SEQUENCE: 15

Arg Ala His Tyr Asn Ile Val Thr Phe
1               5

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
ggagcggtag cacctcct                                                   18

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ctggttcatc atcgctaatc ac                                              22

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
ttggttaaat gacctgcaac a                                               21

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
gagcgctcac gaacagttg                                                  19

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20
gagacactga tttgtgggaa aga                                             23

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
aaatgacaca tgtcagattg ctg                                             23
```

-continued

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
catggcatca cctctctgac                                               20

<210> SEQ ID NO 23
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 23
aagggccgaa gtgtggta                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
gctgccgtca ttttctgc                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
tctcactggc ccgtcatc                                                 18

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 26
cctctgaccc ttaaggagct tat                                           23

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
cgttgcacag gggagtct                                                 18

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 28
tggagcaaca tgtggaactc                                              20

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 29
cagcagccgg ttaccaag                                                18

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
catccacgtg ttggctca                                                18

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 31
gatcatcttg ctggtgaatg agt                                          23

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
caagtcttct cagcgccata                                              20

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
ggaatcttcc ggctgtagg                                               19

<210> SEQ ID NO 34
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 34
ttttgtatgt attagggtga ggacat                                       26

<210> SEQ ID NO 35
<211> LENGTH: 23
```

```
<212> TYPE: DNA
<213> ORGANISM: Artificial Sequence
<220> FEATURE:
<223> OTHER INFORMATION: synthetic oligonucleotide

<400> SEQUENCE: 35
gcgtgttgac catacaatat gaa                                    23
```